(12) United States Patent
Darty et al.

(10) Patent No.: US 11,399,716 B2
(45) Date of Patent: *Aug. 2, 2022

(54) SYSTEMS AND METHODS FOR PERFORMING AN IMAGING TEST UNDER CONSTRAINED CONDITIONS

(71) Applicant: Hypermed Imaging, Inc., Memphis, TN (US)

(72) Inventors: Mark Anthony Darty, Collierville, TN (US); Dmitry Yudovsky, Los Angeles, CA (US)

(73) Assignee: Hypermed Imaging, Inc., Memphis, TN (US)

( * ) Notice: Subject to any disclaimer, the term of this patent is extended or adjusted under 35 U.S.C. 154(b) by 1181 days.

This patent is subject to a terminal disclaimer.

(21) Appl. No.: 15/476,741

(22) Filed: Mar. 31, 2017

(65) Prior Publication Data

US 2017/0202461 A1  Jul. 20, 2017

Related U.S. Application Data

(63) Continuation of application No. 14/664,791, filed on Mar. 20, 2015, now Pat. No. 9,655,519.

(Continued)

(51) Int. Cl.
*A61B 5/00* (2006.01)
*G06Q 30/02* (2012.01)
(Continued)

(52) U.S. Cl.
CPC .......... *A61B 5/0013* (2013.01); *A61B 5/0075* (2013.01); *A61B 5/0077* (2013.01);
(Continued)

(58) Field of Classification Search
CPC . A61B 5/14552; A61B 5/7203; A61B 5/7278; A61B 2562/0233; A61B 2576/00;
(Continued)

(56) References Cited

U.S. PATENT DOCUMENTS 3,981,590 A   9/1976 Perkins
4,486,657 A   12/1984 Bush
(Continued)

FOREIGN PATENT DOCUMENTS

CN   102906559   1/2013
EP   2359745    8/2011
(Continued)

*Primary Examiner* — Shahdeep Mohammed
(74) *Attorney, Agent, or Firm* — Morgan, Lewis & Bockius LLP

(57) ABSTRACT

An imaging system collects a plurality of images of an extremity of a subject, each collected at a unique spectral band. A physiologic arterial parameter of the extremity is determined from the plurality of images upon image registration. A record of the physiological arterial parameter is recorded in an electronic data store and an indication of the parameter is outputted. The method is performed by a medical professional associated with a temporal clinical expenditure cost in an epoch, for an entity. The product of the (i) epoch and the (ii) temporal clinical expenditure cost is less than a difference between (a) an average or absolute reimbursement associated with the current procedural terminology code by the entity and (b) incidental expenditures associated with the performance of the method.

20 Claims, 13 Drawing Sheets

Clinical Diagnostic Environment 20

Related U.S. Application Data

(60) Provisional application No. 62/090,302, filed on Dec. 10, 2014, provisional application No. 62/090,322, filed on Dec. 10, 2014, provisional application No. 61/969,039, filed on Mar. 21, 2014.

(51) Int. Cl.
*G16H 30/20* (2018.01)
*A61B 5/1455* (2006.01)
*G16Z 99/00* (2019.01)

(52) U.S. Cl.
CPC ..... *A61B 5/14551* (2013.01); *G06Q 30/0283* (2013.01); *G16H 30/20* (2018.01); *G16Z 99/00* (2019.02)

(58) Field of Classification Search
CPC . A61B 2562/04; A61B 5/0077; G06T 7/0012; G06T 2207/10024; G06T 2207/30088
See application file for complete search history.

(56) References Cited

U.S. PATENT DOCUMENTS

| | | |
|---|---|---|
| 4,709,144 A | 11/1987 | Vincent |
| 5,043,571 A | 8/1991 | Hasegawa |
| 5,260,745 A | 11/1993 | Takayanagi |
| 5,276,321 A | 1/1994 | Chang et al. |
| 5,528,368 A | 6/1996 | Lewis et al. |
| 5,769,792 A | 6/1998 | Palcic et al. |
| 5,772,580 A | 6/1998 | Utsui |
| 5,900,942 A | 5/1999 | Spiering |
| 6,081,612 A | 6/2000 | Gutkowicz-Krushin et al. |
| 6,441,356 B1 | 8/2002 | Mandella |
| 6,504,943 B1 | 1/2003 | Sweatt et al. |
| 6,519,040 B1 | 2/2003 | Amos |
| 6,736,507 B2 | 5/2004 | Kudryashov et al. |
| 6,785,000 B2 | 8/2004 | Liang et al. |
| 6,826,424 B1 | 11/2004 | Zeng et al. |
| 7,366,365 B2 | 4/2008 | Carver |
| 7,794,394 B2 | 9/2010 | Frangioni |
| 7,869,038 B2 | 1/2011 | Jones et al. |
| 8,320,650 B2 | 11/2012 | Demos et al. |
| 8,406,835 B2 | 3/2013 | Lucassen et al. |
| 8,406,859 B2 | 3/2013 | Zuzak et al. |
| 8,913,241 B2 | 12/2014 | Bhatia et al. |
| 9,107,624 B2 | 8/2015 | Darty |
| 2002/0049386 A1 | 4/2002 | Yang et al. |
| 2005/0010090 A1 | 1/2005 | Acosta et al. |
| 2005/0046850 A1 | 3/2005 | Chow |
| 2005/0154277 A1 | 7/2005 | Tang et al. |
| 2006/0238643 A1 | 10/2006 | Liao |
| 2007/0100330 A1 | 5/2007 | Tilleman |
| 2007/0153281 A1 | 7/2007 | Gordon |
| 2007/0249913 A1* | 10/2007 | Freeman ............ A61B 5/0059 600/300 |
| 2008/0007729 A1 | 1/2008 | Hagler |
| 2008/0032325 A1 | 2/2008 | DiMarzio et al. |
| 2008/0068604 A1 | 3/2008 | Grassinger et al. |
| 2008/0159653 A1 | 7/2008 | Dunki-Jacobs |
| 2008/0267472 A1 | 10/2008 | Demos |
| 2008/0306337 A1 | 12/2008 | Livingston et al. |
| 2009/0262346 A1 | 10/2009 | Egloff et al. |
| 2009/0309960 A1 | 12/2009 | Park |
| 2010/0182594 A1 | 7/2010 | Carron |
| 2010/0231742 A1 | 9/2010 | Yanada |
| 2010/0245616 A1 | 9/2010 | Yoshino et al. |
| 2010/0245818 A1 | 9/2010 | Viard et al. |
| 2011/0118547 A1 | 5/2011 | Erikawa |
| 2011/0170098 A1 | 7/2011 | Normand |
| 2011/0205536 A1 | 8/2011 | Johnsen et al. |
| 2011/0267610 A1 | 11/2011 | Hu et al. |
| 2012/0085932 A1 | 4/2012 | Themelis |
| 2012/0115214 A1 | 5/2012 | Battrell |
| 2012/0140240 A1 | 6/2012 | Hillman et al. |
| 2012/0301068 A1 | 11/2012 | Meade et al. |
| 2013/0128227 A1 | 5/2013 | Cui et al. |
| 2013/0222603 A1 | 8/2013 | Agranov et al. |
| 2013/0300876 A1 | 11/2013 | Lebber |
| 2014/0035703 A1 | 2/2014 | Ma et al. |
| 2014/0078381 A1 | 3/2014 | Ovsiannikov et al. |
| 2014/0112612 A1 | 4/2014 | Tuennermann |
| 2014/0118741 A1 | 5/2014 | Heidrich |
| 2014/0209929 A1 | 7/2014 | Suh |
| 2014/0211199 A1 | 7/2014 | Kuo et al. |
| 2015/0051498 A1 | 2/2015 | Darty |
| 2015/0323384 A1 | 11/2015 | Bird |

FOREIGN PATENT DOCUMENTS

| | | |
|---|---|---|
| WO | WO 2008-100582 | 8/2008 |
| WO | WO 2011-070357 | 6/2011 |
| WO | WO 2011-14280 | 12/2011 |

\* cited by examiner

400

┌─────────────────────────────────────────────────────────────────────┐
│ Collect a plurality of images of a location on an extremity of a subject with  ~402
│ an imaging system, where each respective image in the plurality of images
│ is collected by the imaging system at a unique spectral band in a
│ predetermined set of spectral bands
│
│   The predetermined set of spectral bands is eight to twelve spectral  ~406
│   bands
│
│     The eight to twelve spectral bands include spectral bands having  ~408
│     central wavelengths of 510±2 nm, 530±2 nm, 540±2 nm, 560±2
│     nm, 580±2 nm, 590±2 nm, 620±2 nm, and 660±2 nm;
│     each respective spectral band has a full width at half maximum
│     of less than 10 nm
│
│     The eight to twelve spectral bands include spectral bands having  ~409
│     central wavelengths of 520±2 nm, 540±2 nm, 560±2 nm, 580±2
│     nm, 590±2 nm, 610±2 nm, 620±2 nm, and 640±2 nm;
│     each respective spectral band has a full width at half maximum
│     of less than 10 nm
│
│     The eight to twelve spectral bands include spectral bands having  ~410
│     central wavelengths of 500±1 nm, 530±1 nm, 545±1 nm, 570±1
│     nm, 585±1 nm, 600±1 nm, 615±1 nm, and 640±1 nm;
│     each respective spectral band has a full width at half maximum
│     of less than 10 nm
│
│                                  (A)
└─────────────────────────────────────────────────────────────────────┘

Figure 4A (D)

| | |
|---|---|
| The method is performed by a medical professional in a epoch using the imaging system | 452 |

The medical professional associated with a temporal clinical expenditure cost, and the expression
$$(D * ED) < (RC - IC)$$
is achieved, where:
 D is a duration of the epoch,
 ED is the temporal clinical expenditure cost prorated for the duration of the epoch,
 RC is an average or absolute amount of reimbursement associated with the current procedural terminology code that is receivable by the business entity, and
 IC is the incidental expenditure, other than RC, associated with the medical professional using the electronic device to perform the actions required by the current procedural terminology code — 454

The method includes turning on the imaging system, and the duration of the epoch is less than five minutes — 456

The current procedural terminology code is a medical code associated with:
(i) a noninvasive single level, bilateral physiologic study of the upper or lower extremity arteries of a subject;
(ii) a noninvasive multiple level, complete bilateral physiologic study of upper or lower extremity arteries of a subject; or
(iii) a noninvasive physiologic study of lower extremity arteries of a subject, at rest following treadmill stress testing — 458

Figure 4E

SYSTEMS AND METHODS FOR PERFORMING AN IMAGING TEST UNDER CONSTRAINED CONDITIONS

CROSS REFERENCE TO RELATED APPLICATIONS

This application is a continuation of U.S. patent application Ser. No. 14/664,791, filed Mar. 20, 2015, which claims priority to U.S. Provisional Patent Application No. 61/969,039, filed Mar. 21, 2014, U.S. Provisional Patent Application No. 62/090,302, filed Dec. 10, 2014, and U.S. Provisional Patent Application No. 62/090,322, filed Dec. 10, 2014, the disclosures of which are hereby incorporated by reference herein in their entireties for all purposes.

TECHNICAL FIELD

The present disclosure generally relates to hyperspectral spectroscopy, and in particular, to systems, methods and devices for performing medical imaging under constrained conditions.

BACKGROUND

Medical conditions associated with irregular blood flow to the extremities of a subject, including peripheral arterial disease ("PAD"), diabetic foot ulcers, and critical limb ischemia ("CLI"), are diagnosed using a number of invasive and non-invasive procedures. These procedures include ankle-brachial index (ABI) measurement, plethysmography, transcutaneous oxygen tension (TcPo2) measurements Doppler and ultrasound imaging, computed tomographic angiography (CT), magnetic resonance angiography (MRA), angiography. Each of these procedures, however, provides incomplete information on the underlying condition.

ABI, for example, provides an indication of narrowing or blockage of arteries supplying a subject's legs by measuring differences between a patient's blood pressure at their arms and ankles. However, the procedure does not measure the oxygenation level of the blood flowing to the extremities, the distribution of oxygen at an affected tissue, or the efficiency of oxygen delivery to the tissue. Similarly, plethysmography, Doppler, ultrasound imaging, CT imaging, and MRA imaging provide an indication of the arterial capacity or actual blood flow at the extremities, without providing information on the oxygenation level of the blood flowing to the extremities, the distribution of oxygen at the affected tissue, or the efficiency of oxygen delivery to the tissue. TcPo2, on the other hand, measures the level of oxygenation at a single point below the skin, but does not measure global blood flow, distribution of oxygen at an affected tissue, or the efficiency of oxygen delivery to the tissue.

As such, these techniques provide a medical professional with incomplete information for diagnosing and treating conditions associated with irregular blood flow or lack of adequate oxygen delivery to an affected site. However, use of these techniques is propagated by medical reimbursement schemes that set a fixed or capped reimbursement for studies of peripheral arterial function, because of the relative inexpensive nature of these tests, with respect to the costs associated with the medical professional's time, measurement equipment, and incidental expenses. For example, the American Medical Association established a set of codes—the Current Procedural Terminology ("CPT") codes—that classify treatment for medical and surgical procedures, diagnostic tests, laboratory studies, and other medical services rendered to subjects. The codes provide a uniform system for detailing medical, surgical, and diagnostic services provided by a medical professional, to communicate services rendered to third-parties reimbursing the services, e.g., insurers.

The CPT codes associated with peripheral arterial studies include: CPT 93922, used to report noninvasive single level, bilateral physiologic studies of upper or lower extremity arteries; CPT 93923, used to report noninvasive multiple level, complete bilateral physiologic studies of upper or lower extremity arteries; and CPT 93924, used to report noninvasive physiologic studies of lower extremity arteries, at rest following treadmill stress testing. The average reimbursements associated with Current Procedural Terminology ("CPT") codes 93922, 93923, and 93924, however, ranges between only $120 (CPT 93922) and $220 (CPT 93924). This does not provide a medical establishment with much, if any, room or incentive to implement technological advances into the medical exam, constraining medical professionals to use of traditional—but ill-suited methods—for diagnosing conditions associated with irregular blood flow to the extremities.

Hyperspectral (also known as "multispectral") spectroscopy is an imaging technique that integrates multiples images of an object resolved at different spectral bands (i.e., ranges of wavelengths) into a single data structure, referred to as a three-dimensional hyperspectral data cube. Data provided by hyperspectral spectroscopy is often used to identify a number of individual components of a complex composition through the recognition of spectral signatures of the individual components of a particular hyperspectral data cube. As such, hyperspectral imaging is a more appropriate tool for diagnosis and prognosis of medical conditions associated with irregular blood flow to the extremities of a subject because of its capability to provide information related to blood flow, oxygenation levels of blood delivered to the extremities, distribution of oxygen at an affected tissue, and efficiency of oxygen delivery to the tissue.

Despite the great potential clinical value of hyperspectral imaging, several drawbacks have limited the use of hyperspectral imaging in the clinic setting. In particular, current medical hyperspectral instruments are costly because of the complex optics and computational requirements currently used to resolve images at a plurality of spectral bands to generate a suitable hyperspectral data cube. Hyperspectral imaging instruments can also suffer from poor temporal and spatial resolution, as well as low optical throughput, due to the complex optics and taxing computational requirements needed for assembling, processing, and analyzing data into a hyperspectral data cube suitable for medical use. Moreover, because hyperspectral imaging is time consuming and requires complex optical equipment, it is more expensive than the conventional methods. Thus, medical establishments could not afford to employ such technology because of the relatively small reimbursements available for peripheral arterial studies.

Thus, there is an unmet need in the field for methods of fulfilling the requirements for reimbursement under a current procedural terminology code associated with an extremity arterial study of a subject, while providing high power diagnostic and prognostic medical information.

SUMMARY

The above deficiencies and other problems associated with the cost effective implementation of physiologic examination of upper and lower extremity arteries are eliminated or reduced by the disclosed methods. Various implementations of systems, methods, and devices within the scope of the appended claims each have several aspects, no single one of which is solely responsible for the desirable attributes described herein. Without limiting the scope of the appended claims, some prominent features are described herein. After considering this discussion, and particularly after reading the section entitled "Detailed Description" one will understand how the features of various implementations are used to enable improved fulfillment of the requirements for reimbursement under a current procedural terminology code associated with an extremity arterial study of a subject.

In contrast to conventional hyperspectral imaging, where images are collected sequentially using broadband light sources or by sequentially tuning or turning on light sources matching the wavelength of the sequential image being taken, the present disclosure has the advantages of more quickly capturing a complete hyperspectral image, which in turn reduces the computational burden required to phase sequential images. Further, the unique optical architectures enable the disclosed hyperspectral imaging devices to operate from battery power, reducing the time needed to warm up the imaging device, improving the portability of the device, and reducing the time required to collect the image. The reduced imaging and computational time reduce costs associated with the hourly clinical expenditures of medical professionals. The unique optical architectures also allow the device to be handheld, which increases the ease of use and utility. Thus, the disclosure allows medical establishments to employ diagnostically powerful hyperspectral imaging technology in a cost effective manner, in line with approved reimbursement schemes.

In accordance with some embodiments, a method is performed at an imaging system (e.g., a hyperspectral imaging system). The method includes collecting a plurality of images of a location on an extremity of a subject with the imaging system, wherein each respective image in the plurality of images is collected by the imaging system at a unique spectral band in a predetermined set of spectral bands. The method also includes registering the plurality of images with respect to each other, thereby forming a plurality of registered images. The method further includes determining a first physiologic arterial parameter of the location on the extremity of the subject from the plurality of registered images. The method then includes creating a record of the first physiological arterial parameter of the location on the extremity of the subject in an electronic data store. The method further includes outputting an indication of the first physiologic arterial parameter of the location on the extremity of the subject. The method is performed by a medical professional in an epoch using the imaging system. The medical professional associated with a temporal clinical expenditure cost, and the expression:

$$(D^*E_D) < (R_C - I_C) \qquad \text{Equation 1}$$

is achieved, where D is a duration of the epoch, $E_D$ is the temporal clinical expenditure cost prorated for the duration of the epoch, $R_C$ is an average or absolute amount of reimbursement associated with the current procedural terminology code that is receivable by the business entity, and $I_C$ is the incidental expenditure, other than $R_C$, associated with the medical professional using the electronic device to perform the actions required by the current procedural terminology code on the subject.

In one implementation of the first aspect described above, collecting the hyperspectral image includes illuminating the location on the extremity of the subject with a first light, the first light including a first subset of spectral bands in the predetermined set of spectral bands, and concurrently collecting a first subset of images in the plurality of images of the location on the extremity of the subject while illuminated by the first light, each image in the first subset of images collected at a unique spectral band in the first subset of spectral bands.

In one implementation of the first aspect described above, collecting the hyperspectral image further includes illuminating the location on the extremity of the subject with a second light, the second light encompassing a second subset of spectral bands in the predetermined set of spectral bands, where the second subset of spectral bands is different from than the first subset of spectral bands, and concurrently collecting a second subset of images in the plurality of images of the location on the extremity of the subject while illuminated by the second light, each respective image in the second subset of images collected at a unique spectral band in the second subset of spectral bands.

In one implementation of the first aspect described above, the first plurality of spectral bands includes all of the predetermined set of spectral bands.

In one implementation of the first aspect described above, each respective image in the first sub-plurality of images is collected with a unique optical detector in a plurality of optical detectors.

In one implementation of the first aspect described above, each respective image in the first subset of images is collected with a unique optical detector in a plurality of optical detectors, each respective image in the second subset of images is collected with unique optical detector in the plurality of optical detectors, and at least one optical detector in the plurality of optical detectors collects a respective image in the first subset of images and a respective image in the second subset of images.

In one implementation of the first aspect described above, each respective optical detector in the plurality of optical detectors collects a respective image in the first subset of images and a respective image in the second subset of images.

In one implementation of the first aspect described above, the first subset of images has four images and the second subset of images has four images.

In one implementation of the first aspect described above, each respective optical detector in the plurality of optical detectors is covered by a dual-band pass filter.

In one implementation of the first aspect described above, the first physiologic arterial parameter is a two-dimensional map of deoxyhemoglobin concentration, oxyhemoglobin concentration, or an arithmetic combination of deoxyhemoglobin and oxyhemoglobin concentration of the location on the extremity of the subject.

In one implementation of the first aspect described above, creating a record of the first physiological arterial parameter includes transmitting the record to an electronic data store external to the imaging system.

In one implementation of the first aspect described above, the transmitting is wireless transmission.

In one implementation of the first aspect described above, the imaging system is housed in an interior of a casing, and outputting the indication of the first physiologic arterial parameter includes displaying the indication on a display mounted on an exterior of the casing.

In one implementation of the first aspect described above, outputting an indication of the first physiologic arterial parameter includes displaying the two-dimensional map on a display mounted on the exterior of the hyperspectral imaging system.

In one implementation of the first aspect described above, the predetermined set of spectral bands has from eight to twelve spectral bands.

In one implementation of the first aspect described above, the eight to twelve spectral bands includes eight spectral bands having central wavelengths of: (i) 510±1 nm, 530±1 nm, 540±1 nm, 560±1 nm, 580±1 nm, 590±1 nm, 620±1 nm, and 660±1 nm; (ii) 520±1 nm, 540±1 nm, 560±1 nm, 580±1 nm, 590±1 nm, 610±1 nm, 620±1 nm, and 640±1 nm; or (iii) 500±1 nm, 530±1 nm, 545±1 nm, 570±1 nm, 585±1 nm, 600±1 nm, 615±1 nm, and 640±1 nm, and each respective spectral band in the eight spectral bands has a full width at half maximum of less than 10 nm.

In one implementation of the first aspect described above, the predetermined set of spectral bands has eight spectral bands.

In one implementation of the first aspect described above, the eight spectral bands have corresponding central wavelengths of 510±2 nm, 530±2 nm, 540±2 nm, 560±2 nm, 580±2 nm, 590±2 nm, 620±2 nm, and 660±2 nm, and each respective spectral band in the eight spectral bands has a full width at half maximum of less than 10 nm.

In one implementation of the first aspect described above, the eight spectral bands have corresponding central wavelengths of 520±2 nm, 540±2 nm, 560±2 nm, 580±2 nm, 590±2 nm, 610±2 nm, 620±2 nm, and 640±2 nm, and each respective spectral band in the eight spectral bands has a full width at half maximum of less than 10 nm.

In one implementation of the first aspect described above, the imaging system is handheld and battery operated.

In one implementation of the first aspect described above, the current procedural terminology code is CPT code 93922, 93923, or 93924.

In one implementation of the first aspect described above, the current procedural terminology code is selected from: (i) a medical code associated with a noninvasive single level, bilateral physiologic study of the upper or lower extremity arteries of a subject; (ii) a noninvasive multiple level, complete bilateral physiologic study of upper or lower extremity arteries of a subject; and (iii) a noninvasive physiologic study of lower extremity arteries of a subject, at rest following treadmill stress testing.

In one implementation of the first aspect described above, the method includes turning on the imaging system, and the epoch is less than five minutes.

Thus, methods are provided that fulfill the requirements for reimbursement under a current procedural terminology code associated with an extremity arterial study of a subject in a faster, more cost-efficient manner. Such methods may complement or replace convention methods for performing physiologic studies of upper and lower extremity arteries.

BRIEF DESCRIPTION OF THE DRAWINGS

So that the present disclosure can be understood in greater detail, a more particular description may be had by reference to the features of various implementations, some of which are illustrated in the appended drawings. The appended drawings, however, merely illustrate the more pertinent features of the present disclosure and are therefore not to be considered limiting, for the description may admit to other effective features and arrangements.

FIGS. 4A, 4B, 4C, 4D and 4E are flow-diagrams illustrating a method of fulfilling the requirements for reimbursement under a current procedural terminology code associated with an extremity arterial study of a subject according to some implementations.

Figure 1A:
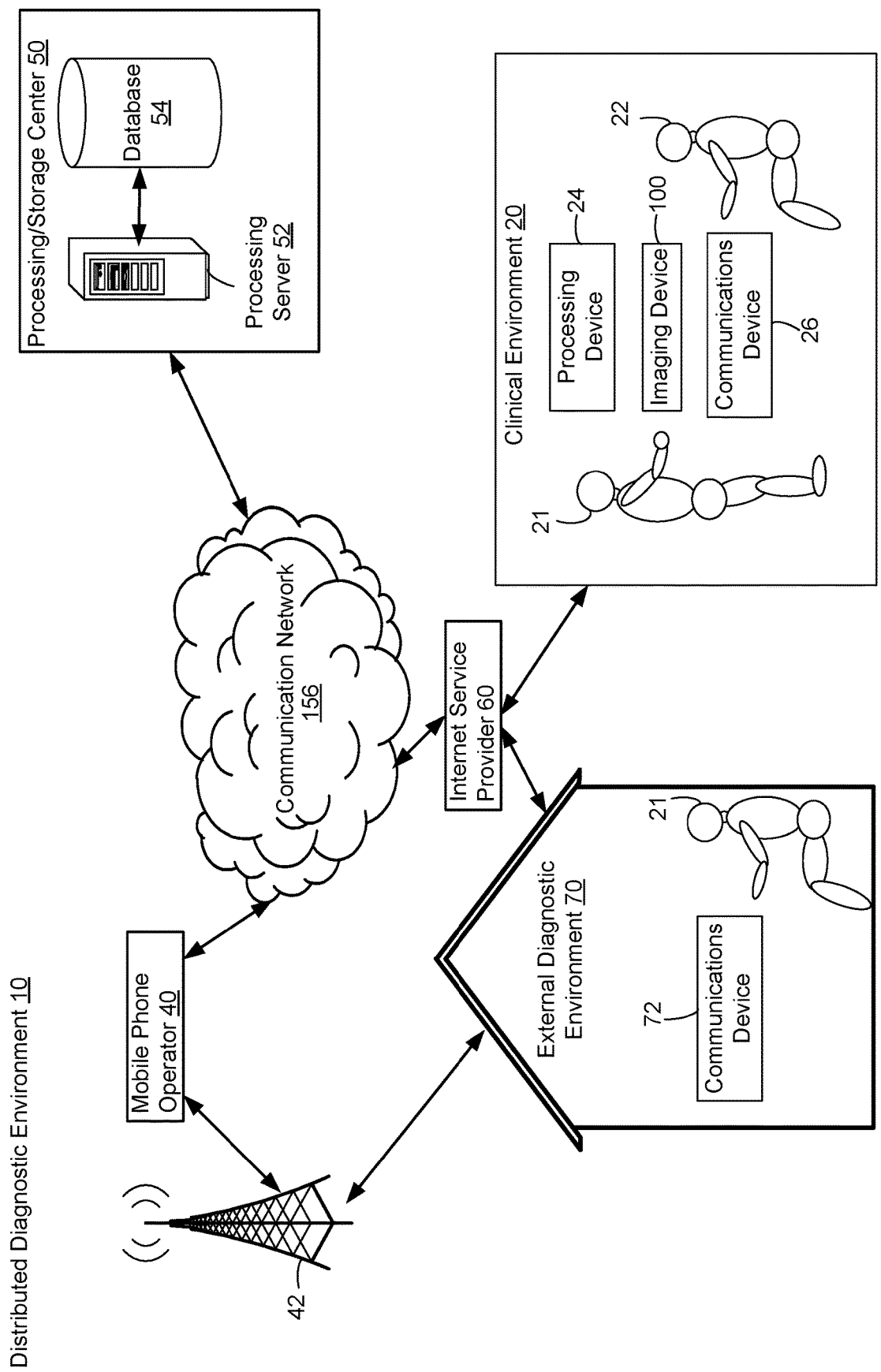
FIG. 1A is a schematic example of a distributed diagnostic environment including a hyperspectral imaging device according to some implementations.

In accordance with common practice the various features illustrated in the drawings may not be drawn to scale. Accordingly, the dimensions of the various features may be arbitrarily expanded or reduced for clarity. In addition, some of the drawings may not depict all of the components of a given system, method or device. Finally, like reference numerals may be used to denote like features throughout the specification and figures.

DETAILED DESCRIPTION

Numerous details are described herein in order to provide a thorough understanding of the example implementations illustrated in the accompanying drawings. However, the invention may be practiced without many of the specific details. And, well-known methods, components, and circuits have not been described in exhaustive detail so as not to unnecessarily obscure more pertinent aspects of the implementations described herein.

One advantage of the present disclosure is that the imaging device collects a hyperspectral image of the location on the extremity of a subject in a very short period of time (e.g., epoch), freeing medical professional to attend to many more patients than possible when relying on older medical imaging and/or noninvasive physiologic testing means. A hyperspectral image may be acquired much more quickly than traditional data is collected. For example, using the strategies disclosed herein, image capture may be achieved in less than one second.

In contrast, data collection for determining ankle/brachial indices takes twenty to thirty minutes, while taking multiple single-point measurements for a transcutaneous oximetry assessment of a foot ulcer can take forty five to sixty minutes. Thus, the disclosed methods increase the throughput capabilities of the clinical environment, improving a subject's access to medical professionals and improving the subject's healthcare by reducing the time before the subject receives appropriate therapy for their medical condition. Similarly, the disclosed methods decrease the cost of healthcare by reducing the cost associated with the medical professional's time spent performing peripheral arterial diagnostics.

Further, hyperspectral imaging provides more complete physiological data for studying tissue oxygenation at the extremities of a subject than do traditional means, such as ankle/brachial indices, volume plethysmography, transcutaneous oxygen measurement, and/or vascular ultrasound. Thus, the disclosed systems and methods provide for more accurate assessment of peripheral arterial function in less time, improving medical diagnosis and decreasing the overall clinical cost.

Figure 1B:
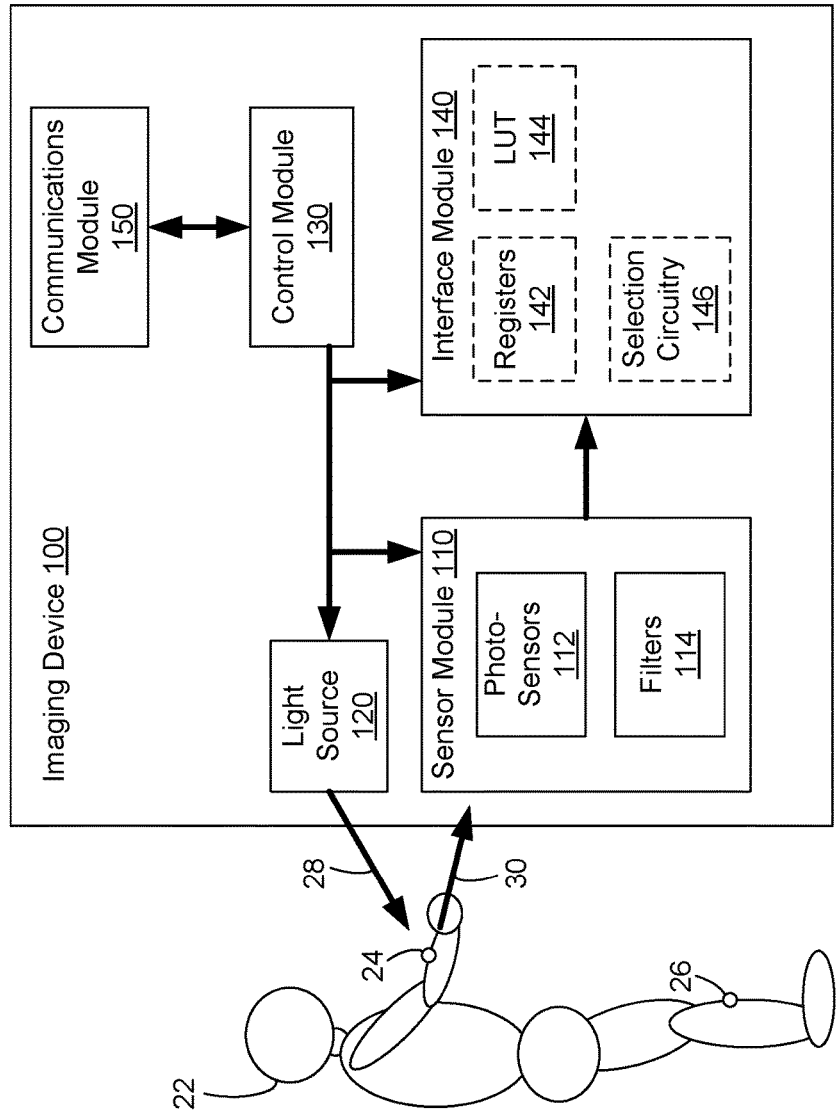
FIG. 1B is a schematic diagram of a local diagnostic environment according to some implementations.
Figure 2:
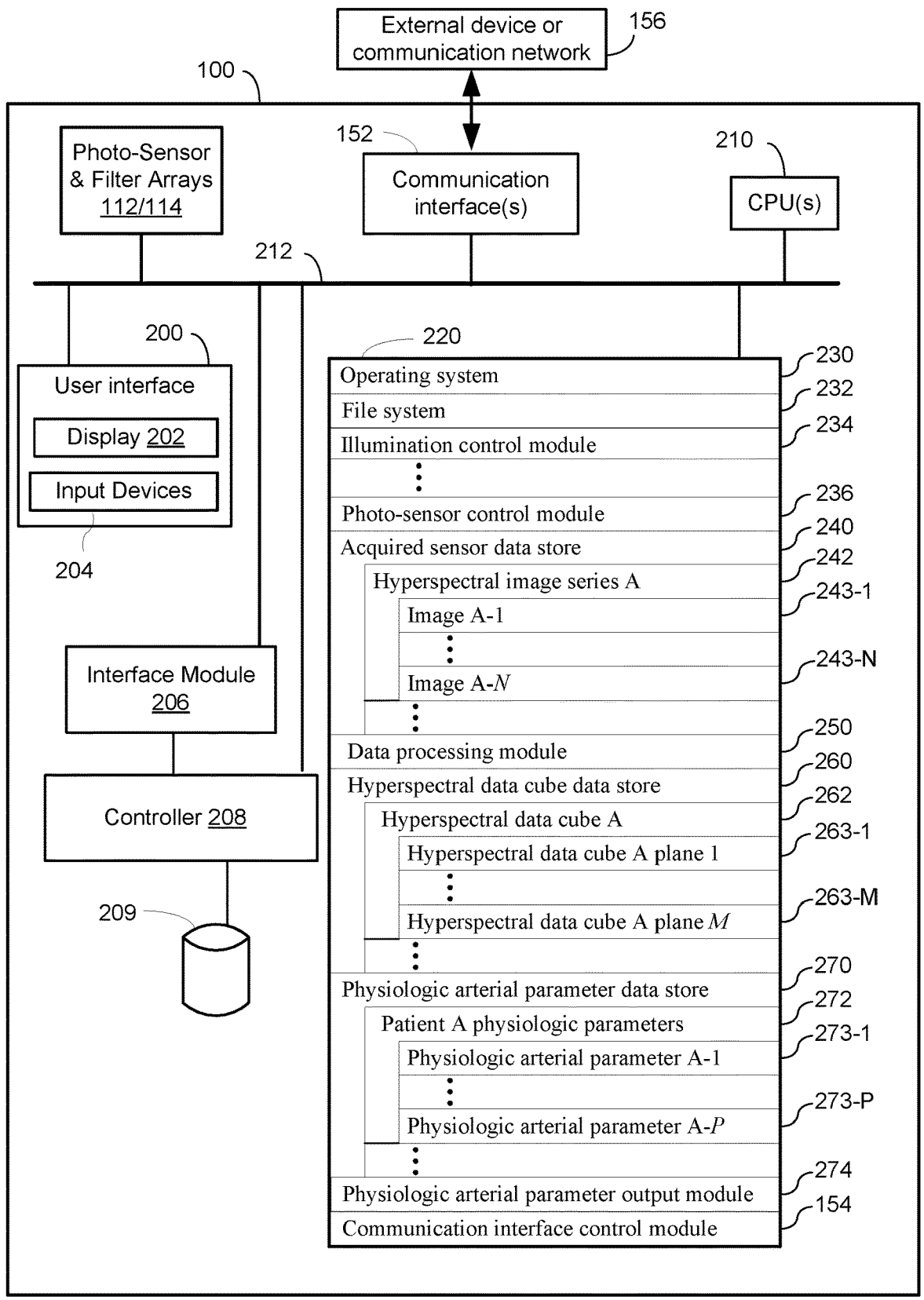
FIG. 2 is a block diagram of an implementation of a hyperspectral imaging device used in accordance with some embodiments of the present disclosure.
Figure 3:
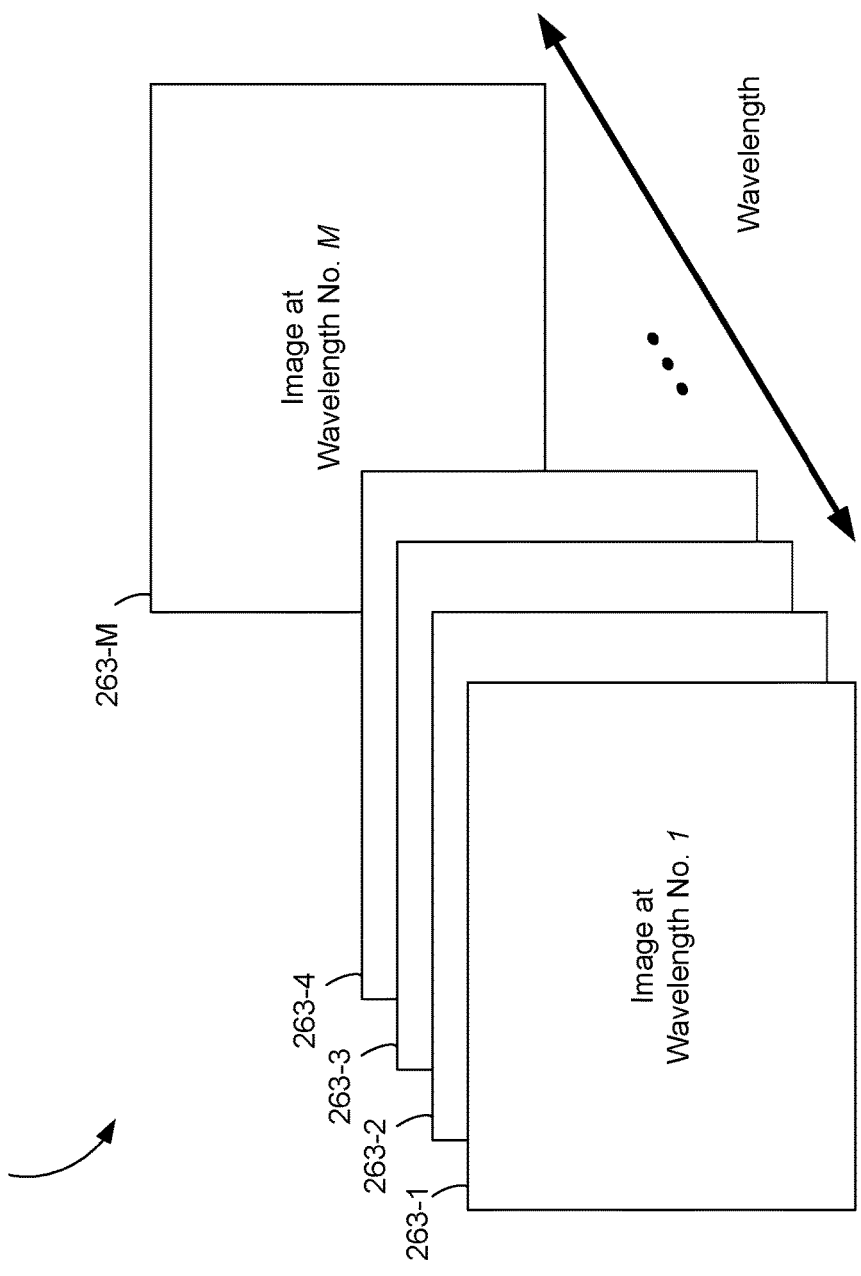
FIG. 3 is a schematic illustration of a hyperspectral data cube.

Below, FIGS. 1-3 provide descriptions of exemplary hyperspectral imaging systems and hyperspectral data cubes for use with the embodiment described herein. FIGS. 4A-4E are flow diagrams illustrating a method of fulfilling the requirements for reimbursement under a current procedural terminology code associated with an extremity arterial study of a subject.

FIG. 1A is an example of a distributed diagnostic environment 10 including an imaging device 100 (e.g., a hyperspectral imaging device) according to some implementations. In some implementations, the distributed diagnostic environment 10 includes one or more clinical environments 20, one or more processing and/or storage centers 50, and a communication network 156 that, together with one or more Internet Service Providers 60 and/or Mobile phone operators 40, with concomitant cell towers 42, allow communication between the one or more clinical environments 20 and the one or more processing and/or storage centers 50.

The clinical environment 20 depicted in FIG. 1 is designed to accommodate the demand of many subjects 22, by taking advantage of improved imaging techniques that speed up diagnostics for medical conditions associated with blood flow to the extremities of a subject 22, e.g., peripheral arterial disease ("PAD"), diabetic foot ulcers, and critical limb ischemia (CLI). In some implementations, the clinical environment 20 includes a medical professional 21 operating an imaging device 100 to collect a hyperspectral image of a location on an extremity of a subject 22. In some embodiments, the clinical environment also includes a communication device 26 that communicates with processing and/or storage center 50 via communications network 156. In some embodiments, the clinical environment 20 includes a processing device 24 for processing hyperspectral images without reliance on processing and/or storage center 50. In some embodiments, the clinical environment includes both a communication device 26 and a processing device 24.

In some implementations, the imaging device 100 illuminates an object (e.g., an area of the body of a subject 22) and generates imaging data of the object. In some implementations, the imaging device 100 illuminates an object using one or more light sources 120. In some implementations, after illuminating the object, or concurrently thereto, the imaging device 100 generates and transmits imaging data (e.g., the hyperspectral image data set) corresponding to the object to processing and/or storage center 50 for forming a processed hyperspectral image. In other implementations, the imaging device 100 and/or processing device 24 form the processed hyperspectral image using the hyperspectral image data set, and transmits the processed hyperspectral image to the processing and/or storage center 50.

In some implementations, resulting images are fully processed by a micro-processor included within the imaging device 100. In some implementations, the resulting processed image(s) is then displayed for the user (e.g., on a display 202 mounted on the exterior of the imaging device or external to the imaging device). In some implementations, the processed image(s) is saved locally (e.g., on imaging device 100). In some implementations, the processed image(s) is sent to a local or remote database (e.g., database 54) via a communication network 156.

In some implementations, image capture and processing includes the imaging device 100 collecting a plurality of images of a location on an extremity of a subject (e.g., a first image captured at a first spectral bandwidth and a second image captured at a second spectral bandwidth). The imaging device 100 stores each respective image at a respective memory location (e.g., the first image is stored at a first location in memory 220 and the second image is stored at a second location in memory 220). Further, the imaging device 100 compares, on a pixel-by-pixel basis (e.g., with processor 210), each pixel of the respective images to produce a hyperspectral image of the location on the extremity of the subject. In some implementations, individual pixel values are binned, averaged, or otherwise arithmetically manipulated prior to pixel-by-pixel analysis, e.g., pixel-by-pixel comparison includes comparison of binned, averaged, or otherwise arithmetically manipulated pixel values.

In some implementations, a physiologic arterial parameter of a location on an extremity of the subject 22 is determined based on the imaging data or processed hyperspectral image at the processing and/or storage center 50, e.g., using processing server 52. In some implementations, a record of the physiologic arterial parameter is created in a database 54 at the processing and/or storage center 50. In some implementations, an indication of the physiologic arterial parameter is sent from the processing and/or storage center 50 back to the clinical environment 20.

In other implementations, a physiologic arterial parameter of a location on an extremity of the subject 22 is determined based on the imaging data or processed hyperspectral image at the clinical environment 20, e.g., using the imaging device 100 and/or processing device 24. In some implementations, an indication of the physiologic arterial parameter is then sent from the clinical environment 20 to the processing and/or storage center 50, where a record is created in database 54. In some implementations, a record of the physiologic arterial parameter is created at a local database in the clinical environment 20. In some implementations, the local database is in the imaging device 100, allowing for optional transfer later to a different local or external database. In other embodiments, the local database is connected wired or wirelessly to the imaging device 100 or processing device 24.

In some implementations, an indication of the physiologic arterial parameter is outputted at the clinical environment for examination by a medical professional 21, which may be the same or different medical professional who operated the imaging device. In some implementations, the indication of the physiological parameter is outputted at an external diagnostics environment 70 including a communications device 72 in communication with the clinical environment 20 and/or processing and/or storage center 50 via the communication network 156.

In some implementations, the medical professional 21, after examining the outputted indication of the physiological parameter, assigns a course of treatment for the subject 22. In some implementations, the treatment may be administered by the same medical professional 21 who operated the imaging device 100, by the medical professional 21 who reviewed the indication of the physiological parameter, by another medical professional 21, or by the subject 22 themselves.

FIG. 1B is a schematic diagram of a clinical diagnostic environment 20 according to some implementations. The clinical diagnostic environment 20 includes an imaging device 100 (e.g., a hyperspectral imaging device) and a communications module 150. The communications module 150 is used, for example, to optionally communicate hyperspectral imaging data to a remote location, to communicate a record of a physiological arterial parameter, and/or to receive software updates or diagnostic information. In some implementations, the imaging device 100 connects to an electronic device (e.g., a PC or laptop) at the clinical diagnostics environment by wired (e.g., USB connection) or wireless connection. The electronic device 100 may function as either, or both, a processing device 24 and communications device 26.

In some implementations, the imaging device 100 illuminates an area of the body of a subject 22 (e.g., a location on an upper extremity 24 or location on a lower extremity 26 of the subject 22) and generates imaging data of the area. In some implementations, the imaging device 100 illuminates the area of the body of the subject using one or more light sources (120). Such light sources emit light 28 that illuminates an area 24 on the subject. Illuminated light penetrating the skin is partially absorbed by chromophores (e.g., hemoglobin and melanin) and partially backscattered to form reflected light 30 that is received by sensor module 110 of imaging device 100. Sensor module 110 includes photo-sensors 112 and filters 114.

In some embodiments, for example, where the imaging device 100 employs a photo-sensory array coupled to a filter array, the output from the photo-sensors 112 is sent to registers 142 of an interface module 140 and processed by one or more register look-up tables 144 and selection circuitry 146. For instance, in some embodiments, look-up table 144 is used in the following manner. In such embodiments, for purposes of illustration, registers 142 is a plurality of registers. The imaging device 100 uses the registers 142 to receive the output of the photo-sensors 112 and the control module 130 identifies which registers 142 in the plurality of registers correspond to filter elements of a particular filter-type in a plurality of filter-types using the look-up table. The control module 130 selects one or more subsets of photo-sensor outputs from the plurality of registers based on the identification of the registers that correspond to filter elements of the particular filter-type. The independent subsets of photo-sensors are then used to form independent images, each image corresponding to a filter-type. To this end, in some implementations there is selection control circuitry 146 to select data using column select and row select circuitry. This data is stored and processed in registers 142.

Operation of the light source 120, sensor module 110 and interface module 140 is under the control of control module 130. In some embodiments, as illustrated in FIG. 1B, control module 130, in turn, interacts with a communications module 150 in order to facilitate the acquisition of hyperspectral imaging data from a subject 22.

FIG. 2 is a block diagram of an implementation of an imaging device, such as imaging device 100. In particular FIG. 2 is not limited to any particular configuration of image acquisition modalities, such as the beam-steering embodiments described with respect to FIGS. 5 and 6, the single sensor embodiments described with respect to FIG. 7, and the simultaneous capture on multiple photo-sensors embodiments described with respect to FIG. 8. In fact, FIG. 2 encompasses any form of imaging device provided that the device enables rapid collection of a hyperspectral image in accordance with the methods described in more detail below, e.g., in accordance with the methods described in FIG. 4A-4E.

The methods described herein can be employed with any known hyperspectral/multispectral imaging system. For example, in one embodiment, the methods described herein are employed in conjunction with a spatial scanning HSI system. Spatial scanning HSI systems include point scanning and line-scanning imaging systems in which a complete spectrum is simultaneously acquired at a single pixel or line of pixels. The instrument then scans through a region of interest collecting complete spectrums at each point (e.g., pixel) or line (e.g., line of pixels) sequentially. In another embodiment, the methods described herein are employed in conjunction with a spectral scanning HSI system. Spectral scanning HSI systems acquire an image of the entire region of interest at a single wavelength with a two-dimensional detector. The instrument collects a series of images of the entire region of interest as each wavelength in a predetermined set of wavelengths.

As such, FIG. 2 encompasses a broad range of imaging devices, provided they are capable of collecting hyperspectral images in the manner disclosed herein. As such, FIG. 2 represents, by way of example and upon adaption to perform the methods disclosed herein, any of the hyperspectral imaging devices of FIGS. 5 through 8 described below, and/or any of the hyperspectral imaging devices disclosed in International Patent Publication Nos. WO 2014/007869, WO 2013/184226, WO 2014/063117, and WO 2014/146053, each of which is hereby incorporated by reference herein in its entirety.

While some example features are illustrated in FIG. 2, those skilled in the art will appreciate from the present disclosure that various other features have not been illustrated for the sake of brevity and so as not to obscure more pertinent aspects of the example implementations disclosed herein. To that end, the imaging device 100 includes one or more central processing units (CPU) 210, an optional main non-volatile storage unit 209, an optional controller 208, a system memory 220 for storing system control programs, data, and application programs, including programs and data optionally loaded from the non-volatile storage unit 209. In some implementations the non-volatile storage unit 209 includes a memory card, for storing software and data. The storage unit 209 is optionally controlled by the controller 208.

In some implementations, the imaging device 100 optionally includes a user interface 200 including one or more input devices 204 (e.g., a touch screen, buttons, or switches) and/or an optional display 202. Additionally and/or alternatively, in some implementations, the imaging device 100 may be controlled by an external device such as a handheld device, a smartphone (or the like), a tablet computer, a laptop computer, a desktop computer, and/or a server system. To that end, the imaging device 100 includes one or more communication interfaces 152 for connecting to any wired or wireless external device or communication network (e.g. a wide area network such as the Internet) 156. In some embodiments imaging device 100 is very compact and docks directly onto or with a handheld device, a smartphone (or the like), a tablet computer, and/or a laptop computer by an electronic interface. In some implementations, imaging device 100 docks to a desktop computer (e.g., via a docking station or USB connection. The imaging device 100 includes an internal bus 212 for interconnecting the aforementioned elements. The communication bus 212 may include circuitry (sometimes called a chipset) that interconnects and controls communications between the aforementioned components.

In some implementations, the imaging device 100 communicates with a communication network 156, thereby enabling the imaging device 100 to transmit and/or receive data between mobile communication devices over the communication network, particularly one involving a wireless link, such as cellular, WiFi, ZigBee, BlueTooth, IEEE 802.11b, 802.11a, 802.11g, or 802.11n, etc. The communication network can be any suitable communication network configured to support data transmissions. Suitable communication networks include, but are not limited to, cellular networks, wide area networks (WANs), local area networks (LANs), the Internet, IEEE 802.11b, 802.11a, 802.11g, or 802.11n wireless networks, landline, cable line, fiber-optic line, USB, etc. The imaging system, depending on an embodiment or desired functionality, can work completely offline by virtue of its own computing power, on a network by sending raw or partially processed data, or both concurrently.

The system memory 220 includes high-speed random access memory, such as DRAM, SRAM, DDR RAM, or other random access solid state memory devices; and typically includes non-volatile memory flash memory devices, or other non-transitory solid state storage devices. The system memory 220 optionally includes one or more storage devices remotely located from the CPU(s) 508. The system memory 220, or alternately the non-transitory memory device(s) within system memory 220, comprises a non-transitory computer readable storage medium.

In some implementations, operation of the imaging device 100 is controlled primarily by an operating system 530, which is executed by the CPU 210. The operating system 230 can be stored in the system memory 220 and/or storage unit 209. In some embodiments, the image device 100 is not controlled by an operating system, but rather by some other suitable combination of hardware, firmware and software.

In some implementations, the system memory 220 includes one or more of a file system 232 for controlling access to the various files and data structures described herein, an illumination software control module 234 for controlling a light source associated and/or integrated with the imaging device 100, a photo-sensor control module 236, a sensor data store 240 for storing hyperspectral image series A 242, including images A-1 243-1 to A-N 243-N, acquired by hyperspectral photo-sensors (e.g. the photo-sensors 112), a data processing software module 250 for manipulating the acquired sensor data, a hyperspectral data cube data store 260 for storing hyperspectral data cube A data 262, including data planes A-1 263-1 to A-M 263-M, assembled from the acquired hyperspectral image series, a physiologic arterial parameter data store 270 for storing physiologic arterial parameters 272, including individual parameters A-1 273-1 to A-P 273-P, determined from the hyperspectral data cube, a physiological arterial parameter output module 274 for outputting one or more of the determined physiologic arterial parameters, and a communication interface software control module 154 for controlling the communication interface 152 that connects to an external device (e.g., a handheld device, laptop computer, or desktop computer) and/or communication network (e.g. a wide area network such as the Internet).

The acquired sensor data 242 and hyperspectral data cube data 262 can be stored in a storage module in the system memory 220, and do not need to be concurrently present, depending on which stages of the analysis the imaging device 100 has performed at a given time. In some implementations, prior to imaging a subject and after communicating the acquired sensor data or processed data files thereof, the imaging device 100 contains neither acquired sensor data 242 nor the hyperspectral data cube data 262. In some implementations, after imaging a subject and after communicating the acquired sensor data or processed data files thereof, the imaging device 100 retains the acquired sensor data 242 and/or hyperspectral data cube data 262 for a period of time (e.g., until storage space is needed, for a predetermined amount of time, etc.).

In some implementations, the programs or software modules identified above correspond to sets of instructions for performing a function described above. The sets of instructions can be executed by one or more processors, e.g., a CPU(s) 210. The above identified software modules or programs (e.g., sets of instructions) need not be implemented as separate software programs, procedures, or modules, and thus various subsets of these programs or modules may be combined or otherwise re-arranged in various embodiments. In some embodiments, the system memory 220 stores a subset of the modules and data structures identified above. Furthermore, the system memory 220 may store additional modules and data structures not described above.

The system memory 220 optionally also includes one or more of the following software modules, which are not illustrated in FIG. 2: a spectral library which includes profiles for a plurality of medical conditions, a spectral analyzer software module to compare measured hyperspectral data to a spectral library, control modules for additional sensors, information acquired by one or more additional sensors, an image constructor software module for generating a hyperspectral image, a hyperspectral image assembled based on a hyperspectral data cube and optionally fused with information acquired by an additional sensor, a fusion software control module for integrating data acquired by an additional sensor into a hyperspectral data cube, and a display software control module for controlling a built-in display.

While examining a subject and/or viewing hyperspectral images of the subject, a physician can optionally provide input to the image device 100 that modifies one or more parameters upon which a hyperspectral image and/or diagnostic output is based. In some implementations, this input is provided using input device 204. Among other things, the image device can be controlled to modify the spectral portion selected by a spectral analyzer (e.g., to modify a threshold of analytical sensitivity) or to modify the appearance of the image generated by an image assembler (e.g., to switch from an intensity map to a topological rendering).

In some implementations, the imaging device 100 can be instructed to communicate instructions to an imaging subsystem to modify the sensing properties of the photo-sensors 112 (e.g., an exposure setting, a frame rate, an integration rate, or a wavelength to be detected). Other parameters can also be modified. For example, the imaging device 100 can be instructed to obtain a wide-view image of the subject for screening purposes, or to obtain a close-in image of a particular region of interest.

In some implementations, the imaging device 100 does not include a controller 209 or storage unit 209. In some such implementations, the memory 220 and CPU 210 are one or more application-specific integrated circuit chips (ASICs) and/or programmable logic devices (e.g. an FGPA—Field Programmable Gate Array). For example, in some implementations, an ASIC and/or programmed FPGA includes the instructions of the illumination control module 234, photo-sensor control module 236, the data processing module 250, physiologic arterial parameter output module 274, and/or communication interface control module 154. In some implementations, the ASIC and/or FPGA further includes storage space for the acquired sensor data store 240 and the sensor data 242 stored therein and/or the hyperspectral data cube data store 260 and the hyperspectral/multispectral data cubes 262 stored therein.

In some implementations, the system memory 220 includes a spectral library and a spectral analyzer for comparing hyperspectral data generated by the image device 100 to known spectral patterns associated with various physiologic arterial parameters and/or medical conditions. In some implementations, analysis of the acquired hyperspectral data is performed on an external device such as a handheld device, tablet computer, laptop computer, desktop computer, an external server, for example in a cloud computing environment or processing and/or storage center 50.

In some implementations, a spectral library includes profiles for a plurality of physiologic arterial parameters and/or medical conditions, each of which contain a set of spectral characteristics unique to the medical condition. A spectral analyzer uses the spectral characteristics to determine the probability that a region of the subject corresponding to a measured hyperspectral data cube is afflicted with the physiologic arterial parameter and/or medical condition. In some implementations, each profile includes additional information about the physiological parameter and/or condition, e.g., information about whether the condition is malignant or benign, options for treatment, etc. In some implementations, each profile includes biological information, e.g., information that is used to modify the detection conditions for subjects of different skin types. In some implementations, the spectral library is stored in a single database. In other implementations, such data is instead stored in a plurality of databases that may or may not all be hosted by the same computer, e.g., on two or more computers addressable by wide area network. In some implementations, the spectral library is electronically stored in the storage unit 220 and recalled using the controller 208 when needed during analysis of hyperspectral data cube data.

In some implementations, the spectral analyzer analyzes a particular spectra derived from hyperspectral data cube data, the spectra having pre-defined spectral ranges (e.g., spectral ranges specific for a particular physiologic arterial parameter and/or medical condition), by comparing the spectral characteristics of a pre-determined physiologic arterial parameter and/or medical condition to the subject's spectra within the defined spectral ranges. In some implementations, the pre-defined spectral ranges correspond to values of one or more of deoxyhemoglobin levels, oxyhemoglobin levels, total hemoglobin levels, oxygen saturation, oxygen perfusion, hydration levels, total hematocrit levels, melanin levels, and collagen levels of a tissue on a patient (e.g., an area 24 or 26 of the body of a subject 22). Performing such a comparison only within defined spectral ranges can both improve the accuracy of the characterization and reduce the computational power needed to perform such a characterization.

In some implementations, the physiologic arterial parameter is selected from the group consisting of blood flow (e.g., blood ingress and/or egress), oxygen delivery, oxygen utilization, oxygen saturation, deoxyhemoglobin levels, oxyhemoglobin levels, total hemoglobin levels, oxygen perfusion, hydration levels, and total hematocrit levels.

In some implementations, the medical condition is selected from the group consisting of peripheral arterial disease (PAD), critical limb ischemia, ulceration, gangrene, tissue ischemia, ulcer formation, ulcer progression, pressure ulcer formation, pressure ulcer progression, diabetic foot ulcer formation, diabetic foot ulcer progression, venous stasis, venous ulcer disease, infection, shock, cardiac decompensation, respiratory insufficiency, hypovolemia, the progression of diabetes, congestive heart failure, sepsis, dehydration, hemorrhage, hypertension, exposure to a chemical or biological agent, and an inflammatory response.

In some implementations, the spectral analyzer identifies a spectral signature within the hyperspectral data cube that corresponds with a physiologic arterial parameter and/or medical condition of the patient. In certain implementations, this is accomplished by identifying a pattern of oxidation or hydration in a tissue associated with a tissue of the patient. In some implementations, the analysis of the hyperspectral data cube includes performing at least one of adjusting the brightness of at least one of the respective digital images in the hyperspectral data cube (e.g., data cube plane 362-M at wavelength range No. M), adjusting the contrast of at least one of the respective digital images in the hyperspectral data cube, removing an artifact from at least one of the respective digital images in the hyperspectral data cube, processing one or more sub-pixels of at least one of the respective digital images in the hyperspectral data cube, and transforming a spectral hypercube assembled from a plurality of digital images.

In some implementations, the display 202 receives an indication of a physiologic arterial parameter from the physiologic arterial parameter output module 274, and displays the indication of the physiologic arterial parameter. In some embodiments, the physiologic arterial parameter output module 274 is a general display control module. In some implementations, the display 202 receives an image (e.g., a color image, mono-wavelength image, or hyperspectral/multispectral image) from a display control module, and displays the image. Optionally, the display subsystem also displays a legend that contains additional information. For example, the legend can display information indicating the probability that a region has a particular medical condition, a category of the condition, a probable age of the condition, the boundary of the condition, information about treatment of the condition, information indicating possible new areas of interest for examination, and/or information indicating possible new information that could be useful to obtain a diagnosis, e.g., another test or another spectral area that could be analyzed.

In some implementations, a housing display is built into the housing of the imaging device 100. In an example of such an implementation, a video display in electronic communication with the processor 210 is included. In some implementations, the housing display is a touch screen display that is used to manipulate the displayed image and/or control the image device 100.

In some implementations, the communication interface 152 comprises a docking station for a mobile device having a mobile device display. A mobile device, such as a smart phone, a personal digital assistant (PDA), an enterprise digital assistant, a tablet computer, an IPOD, a digital camera, a portable music player, or a wearable technology device can be connected to the docking station, effectively mounting the mobile device display onto the imaging device 100. Optionally, the mobile device is used to manipulate the displayed image and/or control the image device 100. In some implementations, the mobile device is used to load software updates or new software onto the imaging device 100.

In some implementations, the communication interface 152 comprises a docking station for a desktop or laptop computer having a display. Optionally, the desktop or laptop computer is used to manipulate the displayed image and/or control the image device 100. In some implementations, the desktop or laptop computer is used to load software updates or new software onto the imaging device 100.

In some implementations, the imaging device 100 is configured to be in wired or wireless communication with an external display, for example, on a handheld device, tablet computer, laptop computer, desktop computer, television, IPOD, projector unit, or wearable technology device, on which the image is displayed. Optionally, a user interface on the external device is used to manipulate the displayed image and/or control the imaging device 100.

In some implementations, an image can be displayed in real time on the display. The real-time image can be used, for example, to focus an image of the subject, to select an appropriate region of interest, and to zoom the image of the subject in or out. In one embodiment, the real-time image of the subject is a color image captured by an optical detector that is not covered by a detector filter. In some implementations, the imager subsystem comprises an optical detector dedicated to capturing true color images of a subject. In some implementations, the real-time image of the subject is a mono-wavelength, or narrow-band (e.g., 10-50 nm), image captured by an optical detector covered by a detector filter. In these embodiments, any optical detector covered by a detector filter in the imager subsystem may be used for: (i) resolving digital images of the subject for integration into a hyperspectral data cube, and (ii) resolving narrow-band images for focusing, or otherwise manipulating the optical properties of the imaging device 100.

In some implementations, an indication of a physiologic arterial parameter and/or hyperspectral image constructed from data collected by the photo-sensors 112 is displayed on an internal housing display, mounted housing display, or external display. Assembled hyperspectral data (e.g., present in a hyperspectral/multispectral data cube) is used to create a two-dimensional representation of the imaged object or subject, based on one or more parameters (e.g., a physiologic arterial parameter). An image constructor module, stored in the imaging system memory or in an external device, constructs an image based on, for example, an analyzed spectrum. Specifically, the image constructor creates a representation of information within the spectra. In one example, the image constructor constructs a two-dimensional intensity map in which the spatially-varying intensity of one or more particular wavelengths (or wavelength ranges) within the spectra is represented by a corresponding spatially varying intensity of a visible marker.

In some implementations, the image constructor fuses a hyperspectral image with information obtained from one or more additional sensors. Non-limiting examples of suitable image fusion methods include: band overlay, high-pass filtering method, intensity hue-saturation, principle component analysis, and discrete wavelet transform.

FIG. 3 is a schematic illustration of a hyperspectral data cube 262. Imaging sensors collect information as a set of images, which are referred to herein as hyperspectral data cube planes 263. Each image 263 represents a range of the electromagnetic spectrum and is also known as a spectral band. These images 263 are then combined and form a three-dimensional hyperspectral data cube 262 for processing and analysis.

Figure 4B:
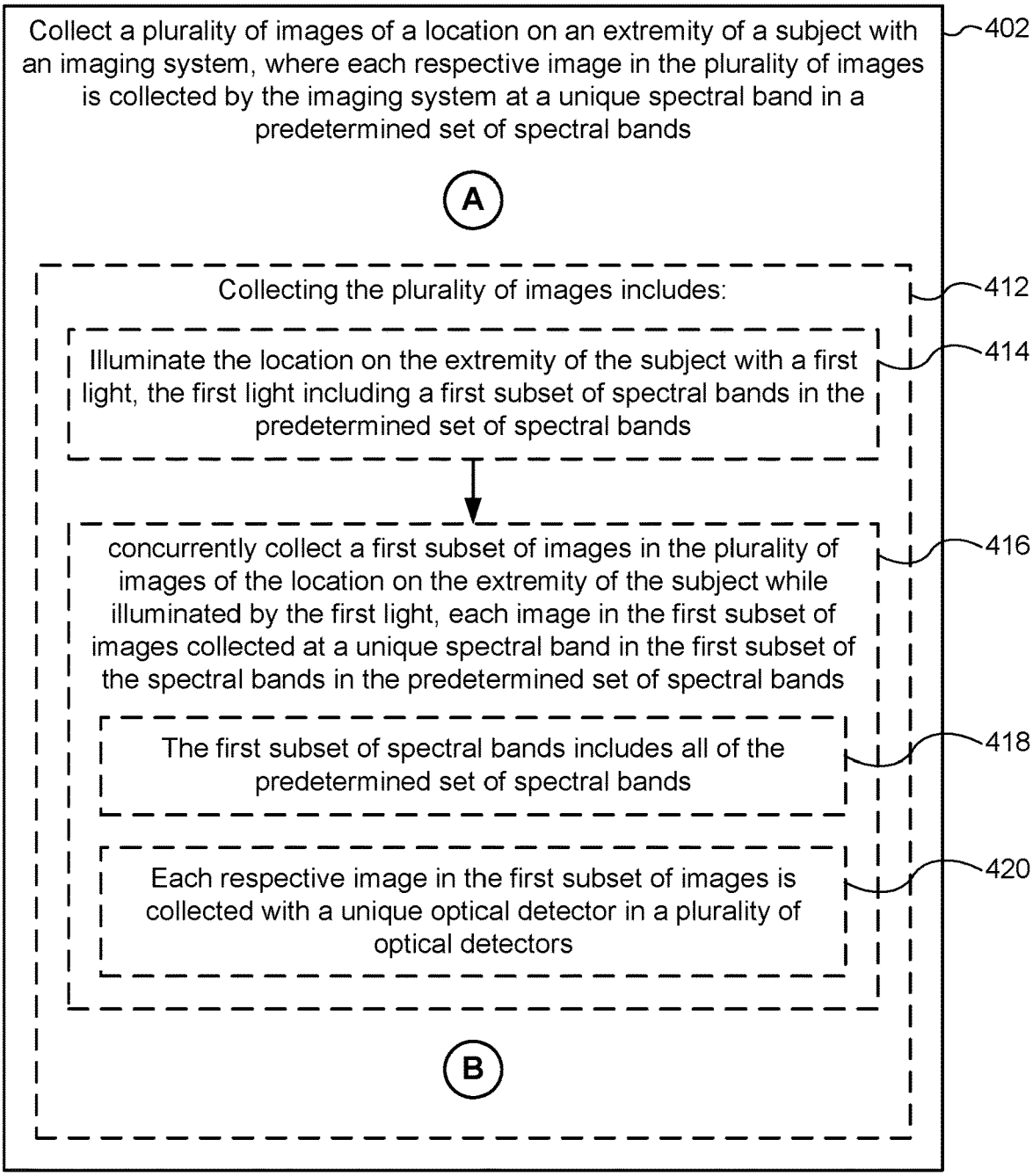
Figure 4C:
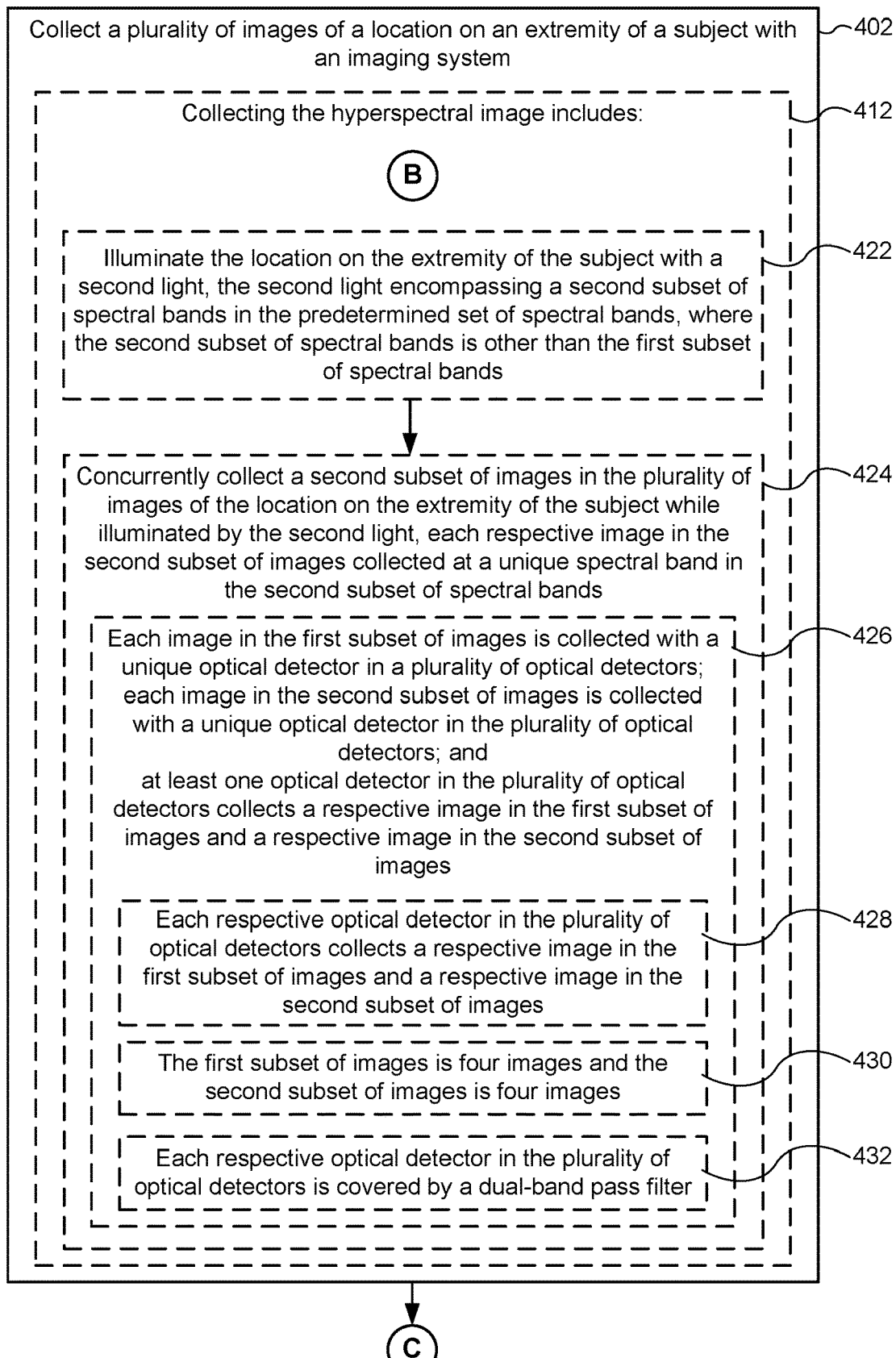
Figure 4D:
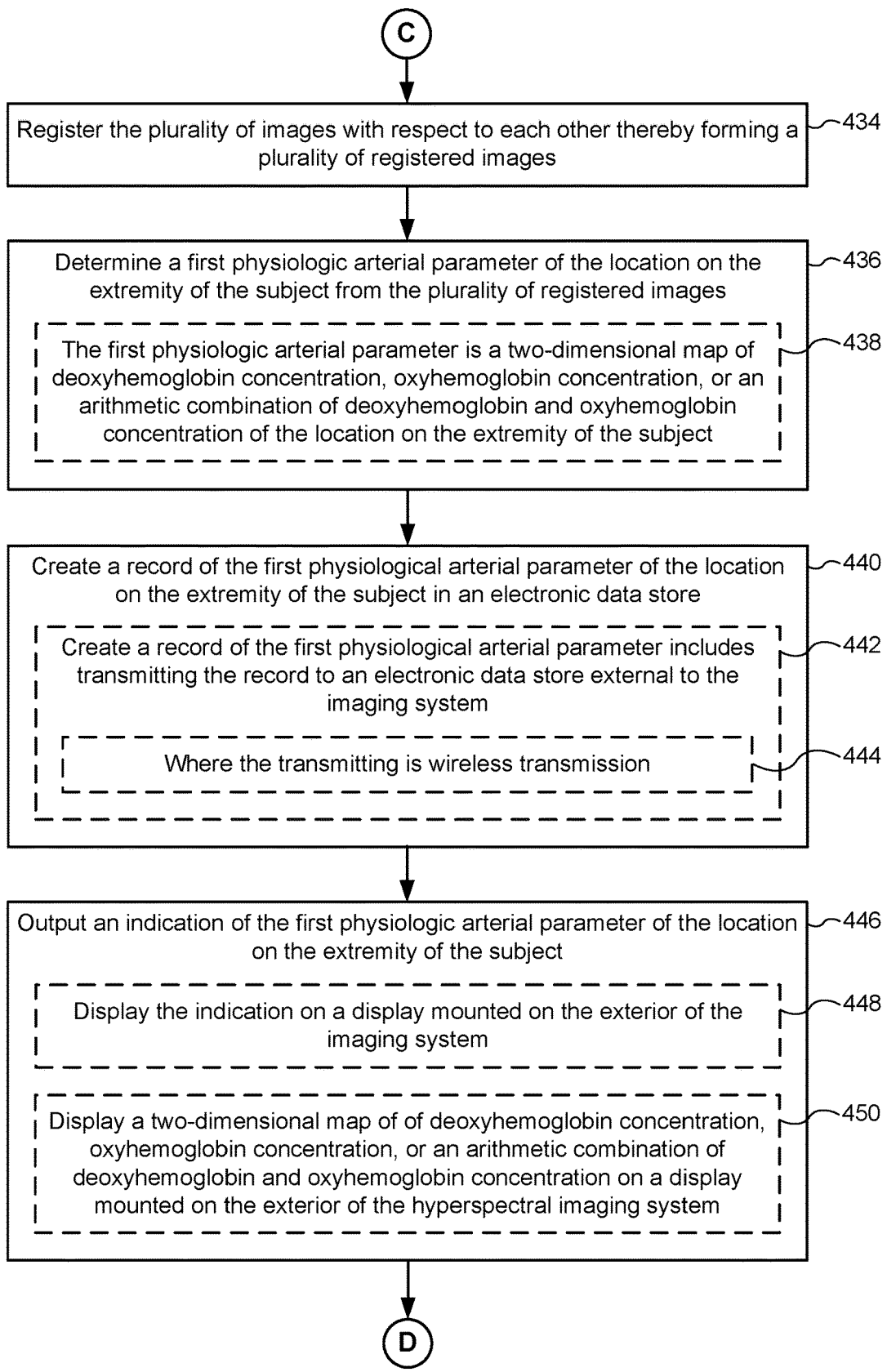

FIGS. 4A-4C are flow diagrams illustrating a method 400 of fulfilling the requirements for reimbursement under a current procedural terminology code associated with an extremity arterial study of a subject. The method 400 is performed at an imaging system (e.g., imaging system 100, FIG. 1; coaxial imaging system 500 employing a beam steering element, FIG. 5; single-sensor imaging system 700 employing photo-sensor and filter arrays, FIG. 7; or simultaneous capture imaging system 800, FIG. 8). As described below, the method allows profitable fulfillment of reimbursement criteria for medical codes related to arterial studies, while providing more accurate diagnostic information than currently employed medical examinations.

The imaging system (e.g., imaging system 100 in FIG. 1; coaxial imaging system 500 employing a beam steering element in FIG. 5; single-sensor imaging system 700 employing photo-sensor and filter arrays in FIG. 7; or simultaneous capture imaging system 800 in FIG. 8), collects (402) a plurality of images (e.g., hyperspectral image series A 242 in FIG. 2) of a location (e.g., location 24 or 26 in FIG. 1B) on an extremity of a subject (e.g., subject 22 in FIGS. 1A-1B), where each respective image in the plurality of images is collected by the imaging system at a unique spectral band (e.g., wavelengths 1 to M in FIG. 3) in a predetermined set of spectral bands In some implementations, the predetermined set of spectral bands is eight to twelve spectral bands (406). In a specific implementation, the predetermined set of spectral bands is eight spectral bands. Although each of the methods described herein may be executed using any number of images, collected at any number of spectral bands, the methods described below are further exemplified using eight images, collected at eight unique spectral bands, for brevity and clarity. However, the methods are in no way limited to use of only eight spectral bands. In some implementations, the predetermined set of spectral bands is 3, 4, 5, 6, 7, 8, 9, 10, 11, 12, 13, 14, 15, 16, 17, 18, 19, 20, or more spectral bands. Each of which is envisioned to be practiced with each of the methods described herein.

In some implementations, each respective spectral band has a full width at half maximum of less than 20 nm. In some implementations, each respective spectral band has a full width at half maximum of less than 10 nm. In some implementations, each respective spectral band has a full width at half maximum of less than 5 nm.

The number and identity of spectral bands employed is dependent upon factors specific to the particular application of hyperspectral imaging. For example, the nature of chromophores of interest in a system (e.g., oxyhemoglobin and deoxyhemoglobin), the nature of chromophores not of interest in a system (e.g., melanin), the desired accuracy (e.g., use of more spectral bands provides greater resolution of chromophores), and the desired speed and cost of acquiring the hyperspectral image (e.g., use of more spectral bands requires more acquisition time and may increase the hardware, acquisition, and/or processing costs).

In some implementations, the predetermined set of spectral bands consists of eight spectral bands having central wavelengths of about 510 nm, 530 nm, 540 nm, 560 nm, 580 nm, 590 nm, 620 nm, and 660 nm.

In a specific implementation, the predetermined set of spectral bands includes eight spectral bands having central wavelengths of 510±2 nm, 530±2 nm, 540±2 nm, 560±2 nm, 580±2 nm, 590±2 nm, 620±2 nm, and 660±2 nm, and each spectral band in the eight spectral bands has a full width at half maximum of less than 10 nm (408).

In some implementations, the predetermined set of spectral bands consists of eight spectral bands having central wavelengths of about 520 nm, 540 nm, 560 nm, 580 nm, 590 nm, 610 nm, 620 nm, and 640 nm.

In another specific implementation, the predetermined set of spectral bands includes eight spectral bands having central wavelengths of 520±2 nm, 540±2 nm, 560±2 nm, 580±2 nm, 590±2 nm, 610±2 nm, 620±2 nm, and 640±2, and each spectral band in the eight spectral bands has a full width at half maximum of less than 10 nm (409).

In some implementations, the predetermined set of spectral bands consists of eight spectral bands having central wavelengths of about 500 nm, 530 nm, 545 nm, 570 nm, 585 nm, 600 nm, 615 nm, and 640 nm.

In another specific implementation, the predetermined set of spectral bands includes eight spectral bands having central wavelengths of 500±1 nm, 530±1 nm, 545±1 nm, 570±1 nm, 585±1 nm, 600±1 nm, 615±1 nm, and 640±1 nm, and each spectral band in the eight spectral bands has a full width at half maximum of less than 10 nm (410).

Use of the term "about," for purposes of this particular set of spectral bands, refers to a central wavelength that is no more than 5 nm from the recited wavelength. In some implementations, each spectral band in the set has a central wavelength that is no more than 4 nm from the recited wavelength. In some implementations, each spectral band in the set has a central wavelength that is no more than 3 nm from the recited wavelength. In some implementations, each spectral band in the set has a central wavelength that is no more than 2 nm from the recited wavelength. In some implementations, each spectral band in the set has a central wavelength that is no more than 1 nm from the recited wavelength. In some implementations, each spectral band in the set has the recited central wavelength.

In some implementations, collecting the plurality of images includes (412): illuminating (414) the location on the extremity of the subject with a first light (e.g., with light source 120 in FIGS. 1B, 5, 6, and 8), the first light including a first subset of spectral bands in the predetermined set of spectral bands. In some implementations, the light used to illuminate the region of interest is polarized to improve the signal-to-noise ratio of backscattered light detected by the imaging system. Use of a polarizing filter, orthogonal to the polarization of the illuminating light, in front of the detector reduces light that is directly reflected off of the target, allowing only back-scattered light to be detected.

In some implementations, collecting the hyperspectral image includes concurrently collecting (416) a first subset of images in the plurality of images of the location on the extremity of the subject (e.g., a subset of images 243 in image series A 242 in FIG. 2) while illuminated by the first light, each image in the first subset of images collected at a unique spectral band in the first subset of the spectral bands in the predetermined set of spectral bands. In other words, images are collected at multiple spectral bands while the region of interest is illuminated with matching light.

Figure 7:
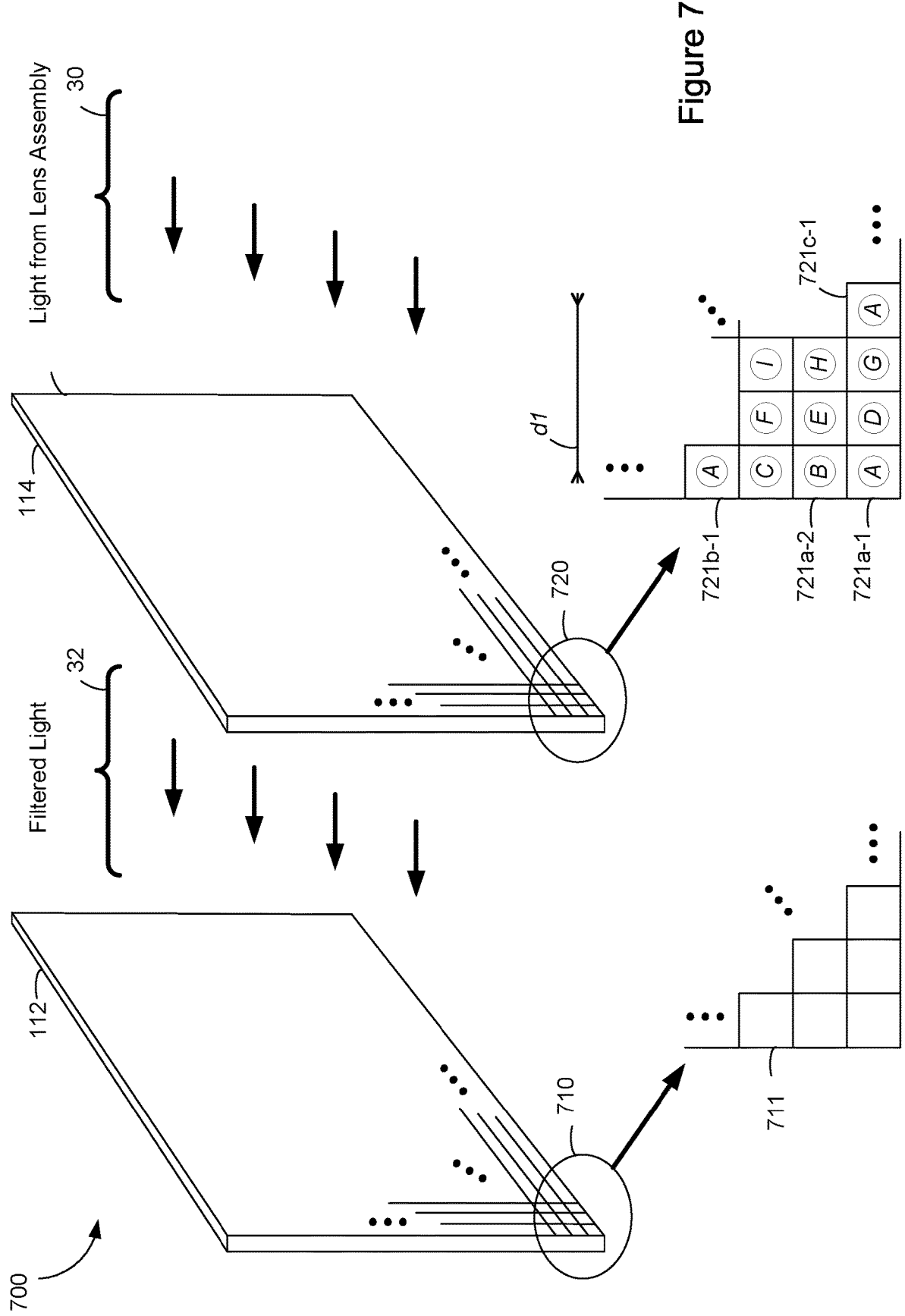
FIG. 7 is an exploded schematic view of an implementation of an image sensor assembly, according to some implementations employing a single-sensor hyperspectral imager.

In some implementations, the first subset of spectral bands includes all of the predetermined set of spectral bands (418). For example, in some implementations, only a single exposure is needed to collect all of the images required to form a hyperspectral image, because they are captured simultaneously. In some embodiments, this is accomplished using a single-sensor imaging system 700 employing a photo-sensor array 710 and filter array 720 (e.g., as illustrated in FIG. 7). In other embodiments, all of the images are captured simultaneously using a simultaneous capture imaging system 800 employing multiple beam splitting elements 810 and detectors 112 covered by unique filters 114 (e.g., as illustrated in FIG. 8).

Figure 8:
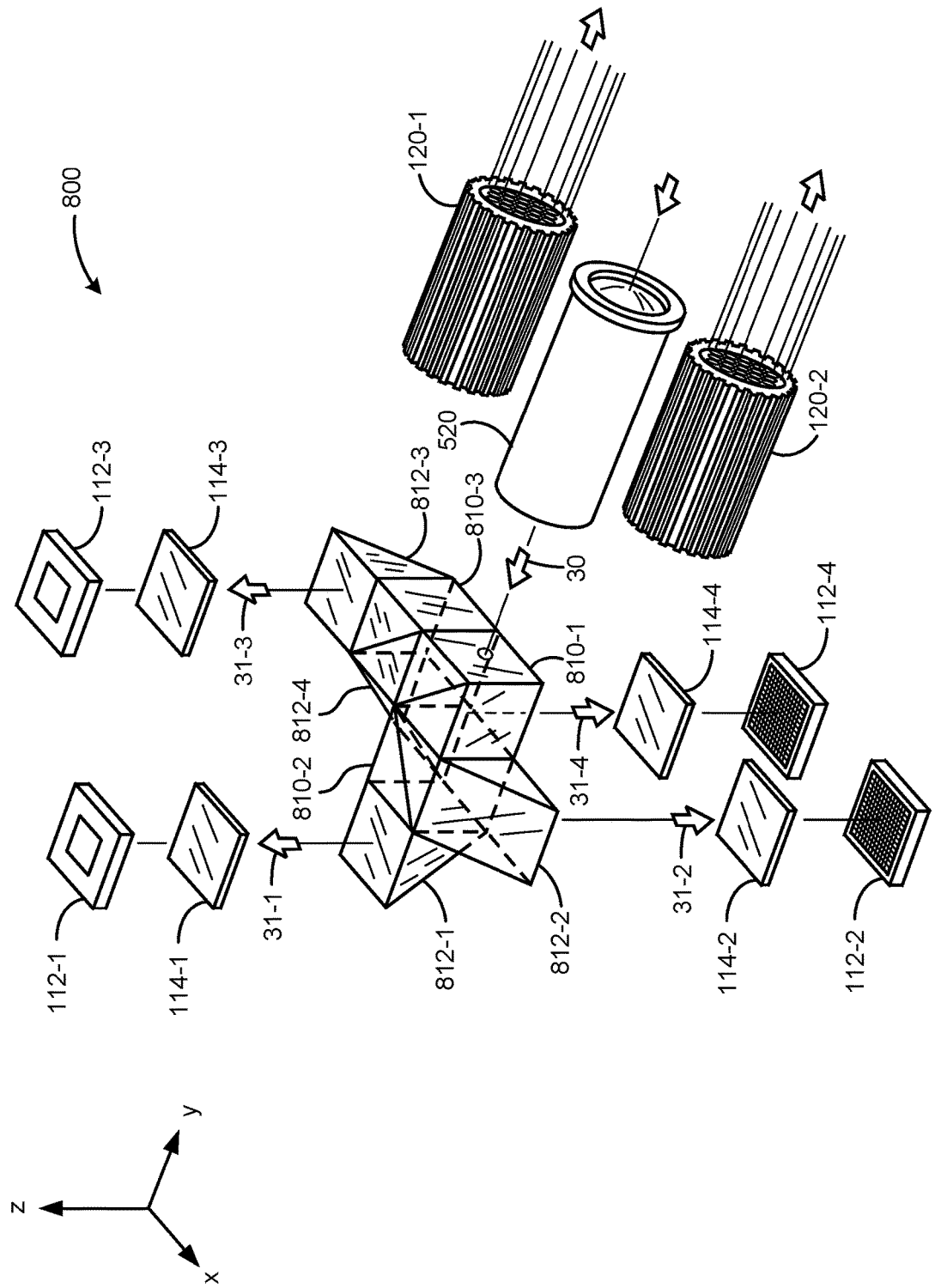
FIG. 8 is an exploded schematic view of a multi-sensor simultaneous capture hyperspectral imaging device, according to some implementations.

In some implementations, each respective image in the first subset of images (e.g., respective images 243 in hyperspectral image series A 242 in FIG. 2) is collected (420) with a unique optical detector in a plurality of optical detectors (e.g., with a respective optical detector 112 in a simultaneous capture imaging system 800 as illustrated in FIG. 8). For example, in some embodiments, each optical detector 112 is covered with a respective filter 114, allowing light corresponding to a unique spectral band in the first plurality of spectral bands to pass to the detector 112. In this fashion, the images simultaneously collected by each of the optical detectors 112 are combined to form a portion of, or the entirety of, image series A 242.

In some implementations, e.g., when images of the subject are collected at less than all of the wavelengths in the predetermined set of spectral bands when illuminated with the first light, the method further includes illuminating (422) the location on the extremity of the subject with a second light (e.g., with light source 120 in FIGS. 1B, 5, 6, and 8), the second light including a second subset of spectral bands in the predetermined set of spectral bands, where the second subset of spectral bands is other than the first subset of spectral bands.

In some implementations, the first light and the second light are irradiated from separate light sources. In some implementations, the light used to illuminate the region of interest is polarized to improve the signal-to-noise ratio of backscattered light detected by the imaging system. Use of a polarizing filter, orthogonal to the polarization of the illuminating light, in front of the detector reduces non-polarized ambient light and light reflected directly off the surface being images from the detected signal.

In some implementations, collecting the hyperspectral image includes concurrently collecting (424) a second subset of images in the plurality of images of the location on the extremity of the subject (e.g., images 243 in image series A 242 in FIG. 2) while illuminated by the second light, each respective image in the second subset of images collected at a unique spectral band in the second subset of spectral bands. In other words, a second set of images is collected at multiple spectral bands while the region of interest is illuminated with matching light. The second set of images complements the first set of images, such that all images required for a hyperspectral image series (e.g., series A 242 in FIG. 2) are collected between the first and second set of images.

In some implementations, each respective image in the first subset of images is collected with a unique optical detector in a plurality of optical detectors, each respective image in the second subset of images is collected with unique optical detector in the plurality of optical detectors, and at least one optical detector in the plurality of optical detectors collects (426) a respective image in the first subset of images and a respective image in the second subset of images. In other words, in some implementations, an imaging system having more than one imaging sensor (e.g., a simultaneous capture imaging system 800, as illustrated in FIG. 8) is used, and at least one of the optical detectors (e.g., optical detector 112-1 in FIG. 8) is used to collect a first image (e.g., in the first subset of images) at a first spectral band and then a second image (e.g., in the second subset of images) at a second spectral band.

In some embodiments, the optical detector (e.g., optical detector 112-1 in FIG. 8) is covered by a dual band pass filter (e.g., filter 114-1 in FIG. 8) that allows light of the first spectral band and light of the second spectral band to pass through to the optical detector. In this fashion, the location on the extremity of the subject is first illuminated with light that includes the first spectral band, but not the second spectral band, and the first image is captured by the optical detector (e.g., optical detector 112-1 in FIG. 8). Then, the location on the extremity of the subject is illuminated with light that includes the second spectral band, but not the first spectral band, and the second image is captures by the optical detector (e.g., the same optical detector 112-1 in FIG. 8). Thus, the optical detector (e.g., optical detector 112-1 in FIG. 8) is used to collect two images, at different spectral bands, of the hyperspectral image series (e.g., image 243-B and image 243-C in image series A 242, represented in FIG. 2).

In some implementations, each respective optical detector in the plurality of optical detectors (e.g., each of optical detectors 112-1 to 112-4, illustrated in FIG. 8) collects (428) a respective image in the first subset of images and a respective image in the second subset of images. In some implementations, each optical detector (e.g., optical detectors 112 in FIG. 8) is covered by a unique dual band pass filter (e.g., filters 114 in FIG. 8). In this fashion, the location on the extremity of the subject is illuminated with a first light having spectral bands corresponding to one of the band passes on each of the filters, but not light having spectral bands corresponding to the other band passes on each of the filters (e.g., light emitted from first light source 120-1). A first sub-set of images is collected while the location is illuminated with the first light. Then, the location is illuminated with a second light having spectral bands corresponding to the other spectral band pass on each of the filters, but not light having wavelengths corresponding to the first band pass on each of the filters (e.g., light emitted from second light source 120-2). A second sub-set of images is then collected while the location is illuminated with the second light.

In some implementations, the first subset of images is four images and the second subset of images is four images (430). For example, in some implementations, an imaging system having four optical detectors (e.g., simultaneous capture imaging system 800 in FIG. 8) is used. Each optical detector (e.g., optical detectors 112) collects an image in the first subset and an image in the second subset of images, to form a hyperspectral image series consisting of eight images.

In some implementations, each respective optical detector in the plurality of optical detectors (e.g., optical detectors 112 of a hyperspectral imaging system such as the simultaneous capture imaging system 800 illustrated in FIG. 8) is covered (432) by a dual-band pass filter (e.g., filters 114 in FIG. 800).

In some implementations, each respective optical detector is covered by a triple band pass filter, enabling use of a third light source and collection of three sets of images at unique spectral bands. For example, four optical detectors can collect images at up to twelve unique spectral bands, when each detector is covered by a triple band-pass filter.

In some implementations, each respective optical detector is covered by a quad-band pass filter, enabling use of a fourth light source and collection of four sets of images at unique spectral bands. For example, four optical detectors can collect images at up to sixteen unique spectral bands, when each detector is covered by a quad band-pass filter. In yet other implementations, band pass filters allowing passage of five, six, seven, or more bands each can be used to collect larger sets of unique spectral bands.

The method further includes, registering (434) the plurality of images with respect to each other thereby forming a plurality of registered images. In some implementations, registering includes storing each respective image at a corresponding memory location (e.g., in memory 220), and comparing, on a pixel-by-pixel basis (e.g., with processor 210) each pixel of the respective images to produce the plurality of registered images. In some implementations, one or more registered images is then stored at a corresponding memory location.

The method further includes, determining (436) a first physiologic arterial parameter (e.g., physiologic arterial parameter 273 in FIG. 2) of the location on the extremity of the subject (e.g., using the data processing module 250 in FIG. 2) from the registered images (e.g., registered images of image series A 242 in FIG. 2). In some implementations, the first physiologic arterial parameter is blood flow (e.g., blood ingress and/or egress), oxygen delivery, oxygen utilization, oxygen saturation, deoxyhemoglobin levels, oxyhemoglobin levels, total hemoglobin levels, oxygen perfusion, hydration levels, total hematocrit levels, or an arithmetic combination thereof In some implementations, the first physiologic parameter is determined at the hyperspectral imaging system (e.g., using the one or more CPU(s) 210). In other implementations, the first physiologic parameter is determined at an exterior processor. In one embodiment, the first physiologic parameter is determined at an external processing device (e.g., processing device 24 in FIG. 1A) within the clinical environment (e.g., at a server located in a clinical environment 20, such as a hospital or clinic, as illustrated in FIG. 1A). In another embodiment, the first physiologic parameter is determined at an external processing device (e.g., processing server 52 in FIG. 1A) located in a remote location (e.g., processing/storage center 50 in FIG. 1A).

In some implementations, where the first physiologic parameter is determined at a remote location, raw image files (e.g., images 243 in hyperspectral image series 242 in FIG. 2) collected at the hyperspectral imaging device (e.g., hyperspectral imaging system 100 in FIG. 1) are sent to the remote location (e.g., via communication network 156 in FIG. 1A). In other implementations, where the first physiologic parameter is determined at a remote location, pre-processed image files (e.g., hyperspectral data cube planes 263 in hyperspectral data cube 262 in FIG. 2) processed locally (e.g., using one or more CPU(s) 210 of hyperspectral imaging system 100 in FIG. 2; or processing device 24 located at clinical environment 20) are sent to the remote location (e.g., via communication network 156 in FIG. 1A).

In one implementation, the first physiologic arterial parameter is a two-dimensional map of deoxyhemoglobin concentration, oxyhemoglobin concentration, or an arithmetic combination of deoxyhemoglobin and oxyhemoglobin concentration of the location on the extremity of the subject (438).

In some implementations, the method further includes creating (440) a record of the first physiological arterial parameter of the location on the extremity of the subject (e.g., records 273 of physiologic arterial parameters 272, as illustrated in FIG. 2) in an electronic data store (e.g., memory 220 in imaging device 100 in FIG. 2; database 54 in processing/storage center 50 in FIG. 1A). In some implementations, the record includes a record of the diagnostic procedure (e.g., collecting the image series of the location on the extremity of the subject) for purposes of billing for medical reimbursement under an approved procedure code (e.g., one or more of current procedural terminology codes 93922, 93923, and 93924). In some implementations, a record of the first physiological arterial parameter of the location on the extremity of the subject is created in a first data store for medical purposes (e.g., in order for a medical professional to refer to at a later time for diagnostic or therapeutic purposes), and a record of the diagnostic procedure performed is created in a second data store (e.g., in a data store associated with the medical billing practices of the clinical environment) for medical reimbursement purposes. In some implementations, the record is created according to pre-programmed instructions. In other implementations, the record is created by manual input (e.g., by a medical professional 21 or clerical professional located in the clinical environment 20 or external diagnostic environment 70, as illustrated in FIG. 1A) into an electronic data store (e.g., at imaging device 100, a data store in clinical environment 20, or database 54 in processing/storage center 50, as illustrated in FIG. 1A).

In some implementations, the method is performed without creating a record of the first physiologic arterial parameter in an electronic data store. For example, in some implementations, a first physiological arterial parameter of the location on the extremity of the subject is determined (e.g., using one or more CPU(s) 210 in imaging system 100, FIG. 2; processing device 24 in the clinical environment 20, FIG. 1A; or processing server 52 in processing/storage center 50, FIG. 1A) and displayed (e.g., on imaging device 100, communications device 26, or an external monitor located in a clinical environment 20, or on communication device 72 located in an external diagnostic environment 70, as illustrated in FIG. 1A) and recorded otherwise (e.g., via a recording device or on paper) by a medical or clerical professional (e.g., medical professional 21 or clerical professional located in the clinical environment 20 or external diagnostic environment 70, as illustrated in FIG. 1A).

In some implementations, creating a record of the first physiological arterial parameter includes transmitting (442) the record to an electronic data store external to the imaging system (e.g., an electronic data store located in clinical environment 20 or a database 54 in a processing/storage center 50, as illustrated in FIG. 1A). In some implementations, the transmitting is wireless transmission (444). In some implementations, the transmitting is wired (e.g., accomplished by connecting the imaging system 100 to a server or communications device 26 located in clinical environment 20, for example by USB connection, as illustrated in FIG. 1A).

The method further includes, outputting (446) an indication of the first physiologic arterial parameter (e.g., physiologic arterial parameter 273) of the location on the extremity of the subject. In some implementations, outputting an indication of the first physiologic arterial parameter includes displaying (448) the indication on a display mounted on the exterior of the imaging system (e.g., on display 202 of imaging system 100; FIG. 2). For example, in some implementations, a medical professional (e.g., medical professional 21 in clinical environment 20; FIG. 1) takes an image series of the location on the extremity of the subject (e.g., subject 22, FIG. 1), the image series is processed to determine a first physiologic arterial parameter (e.g., using one or more CPU(s) 210 in imaging system 100, using a processing device 24 located in the clinical environment 20, or using a processing server located in a remote processing/storage center, as illustrated in FIG. 1A), the first physiologic arterial parameter is optionally transmitted back to the imaging system 100 (e.g., in cases where it is determined external to the system), and displayed on a display integrated with the imaging system 100.

In some implementations, the imaging system 100 is handheld and battery operated. This is accomplished by reducing the power budget needed to operate the imaging system 100. In non-limiting examples, the power budget is reduced by one or more of: using crossed polarizing filters in front of the illumination source (e.g., light source 120 in FIG. 1B; illumination subsystem 510 in FIG. 5; or illumination source 120 in FIG. 8) and detection source (e.g., sensor module 110 in FIG. 1B, optical detectors 112 in FIG. 5 and FIG. 8); using matched narrowband irradiation sources (e.g., LED light sources emitting one or more narrow spectral bands) and detection filters (e.g., notch or other narrow band filters); using capacitors to store large current bursts needed for efficient illumination of the target (e.g., the location on the extremity of the subject); or reducing the number of spectral bands required to construct a high resolution hyperspectral image (e.g., using only eight spectral bands).

In some embodiments, e.g., where the imaging system 100 is handheld, the display is fully integrated within the device (e.g., like a display on a digital camera). In other embodiments, where the imaging system 100 is handheld, the display is detachable from the imaging system. For example, in some implementations, a portable electronic device (e.g., a smart phone, a personal digital assistant (PDA), an enterprise digital assistant, a tablet computer, an IPOD, a digital camera, a portable music player, or a wearable technology device) is docked with the imaging system 100, which displays the indication of the first physiologic arterial parameter on the display of the portable electronic device. In some implementations, the indication of the first physiologic arterial parameter is displayed on an external monitor (e.g., a handheld device, tablet computer, laptop computer, desktop computer, television, IPOD, projector unit, or wearable technology device) located in the clinical environment (e.g., clinical environment 20, FIG. 1A) or in an external diagnostic environment (e.g., external diagnostic environment 70, FIG. 1A).

In some implementations, the indication of the first physiologic arterial parameter is displayed as a two-dimensional map of the location on the extremity of the subject (e.g., a rendering of a portion of the imaged extremity). The two-dimensional map includes information on a physiological parameter (e.g., blood flow (e.g., blood ingress and/or egress), oxygen delivery, oxygen utilization, oxygen saturation, deoxyhemoglobin levels, oxyhemoglobin levels, total hemoglobin levels, oxygen perfusion, hydration levels, total hematocrit levels, or an arithmetic combination thereof) of the subject's tissue. In some implementations, the information on the physiological parameter is represented as a pseudo-colored image.

In one implementation, outputting an indication of the first physiologic arterial parameter includes displaying (450) a two-dimensional map on a display mounted on the exterior of the imaging system 100.

The method is performed (452) by a medical professional (e.g., medical professional 21, FIG. 1A) in an epoch (e.g., a period of time). The medical professional associated (454) with a with a temporal clinical expenditure cost. The expression:

$$(D^* E_D) < (R_C - I_C) \qquad \text{Equation 1}$$

is achieved, where D is a duration of the epoch, $E_D$ is the temporal clinical expenditure cost (e.g., salary and benefits) prorated for the duration of the epoch, $R_C$ is an average or absolute amount of reimbursement associated with the current procedural terminology code that is receivable by the business entity, and $I_C$ is the incidental expenditure (e.g., the cost of office space, insurance, administrative staff), other than $R_C$, associated with the medical professional using the electronic device to perform the actions required by the current procedural terminology code (e.g., in order to fulfill the requirements of the current procedural terminology code).

In some implementations, the first epoch is no more than 15 minutes, preferably no more than 10 minutes, and more preferably no more than 5 minutes. In a specific implementation, the first epoch is less than 5 minutes. In another specific implementation, the method includes turning on the imaging system, and the first epoch is less than five minutes (454). For example, conventional hyperspectral imaging systems are large and heavy, and require high levels of power to operate. These systems are typically mounted on a mobile cart, requiring the user to locate them within the clinical environment, wheel them into subject's room, plug them into an AC power source, turn the instrument on (which can take 5-10 minutes or longer dependent upon, e.g., the hardware/software used to run the system and illumination sources that must be warmed up), and then capture the required images.

The temporal clinical expenditure cost (e.g., an hourly clinical expenditure cost) depends upon many factors, including the level of the professional (e.g., orderly, nurse, physician's assistant, or doctor), the region of the country the clinic is located (e.g., urban or rural), and the economic conditions of the area surrounding the clinic (e.g., affluent or impoverished). For example, the temporal clinical expenditure cost for an orderly, performing a method described herein in a poor, rural town will be much less than the cost associated with a doctor performing the method in a downtown, high-rise office suite located in an affluent city. The reimbursement, however, is regulated by an agency (e.g., the Centers for Medicare & Medicaid Services).

By way of example, assume that a peripheral arterial study is performed by a medical professional associated with a temporal clinical expenditure cost of $400 per hour and the average reimbursement for the study is $120. In one embodiment, the medical professional uses a handheld, imaging system, that does not require calibration before each use, and that captures images at multiple wavebands simultaneously, according to one implementation described herein. The study takes the medical professional five minutes start to finish. The cost associated with the procedure is approximately $35, providing the clinic with a profit of $85. In a second embodiment, the medical professional uses a conventional hyperspectral imaging system, which must wheeled into the room, plugged in, booted-up, and takes three to five minutes to serially acquire each of the images in the series of images needed to construct a hyperspectral image. The study time takes 10 to 15 minutes from start to finish, costing the clinic $70 to $100, and providing little profit from the procedure.

Thus, as compared to the use of conventional hyperspectral imaging, the methods provided herein render hyperspectral imaging practical for use in the clinic. This allows medical professionals to replace use of older techniques having lower diagnostic power with hyperspectral imaging without sacrificing their economic potential.

In some implementations, the current procedural terminology code is a medical code associated with: (i) a noninvasive single level, bilateral physiologic study of the upper or lower extremity arteries of a subject; (ii) a noninvasive multiple level, complete bilateral physiologic study of upper or lower extremity arteries of a subject; or (iii) a noninvasive physiologic study of lower extremity arteries of a subject, at rest following treadmill stress testing CPT code 93922, 93923, or 93924 (458).

CPT code 93922 is used to report noninvasive physiologic studies of upper or lower extremity arteries, single level, bilateral, conventionally performed using, e.g., ankle/brachial indices, Doppler waveform analysis, volume plethysmography, and transcutaneous oxygen tension measurements. CPT code 93923 is used to report noninvasive physiologic studies of upper or lower extremity arteries, multiple levels or with provocative functional maneuvers, complete bilateral study, conventionally performed using, e.g., segmental blood pressure measurements, segmental Doppler waveform analysis, segmental volume plethysmography, segmental transcutaneous oxygen tension measurements, measurements with postural provocative tests, and measurements with reactive hyperemia. CPT code 93924 is used to report noninvasive physiologic studies of lower extremity arteries, at rest following treadmill stress testing.

In some implementations, the method further includes providing a diagnosis of a medical condition based on the first physiological arterial parameter of the location on the extremity of the subject. In some implementations, the medical condition is peripheral arterial disease (PAD), critical limb ischemia, ulceration, gangrene, tissue ischemia, ulcer formation, ulcer progression, pressure ulcer formation, pressure ulcer progression, diabetic foot ulcer formation, diabetic foot ulcer progression, venous stasis, venous ulcer disease, infection, shock, cardiac decompensation, respiratory insufficiency, hypovolemia, the progression of diabetes, congestive heart failure, sepsis, dehydration, hemorrhage, hypertension, exposure to a chemical or biological agent, or an inflammatory response.

In some implementations, the method further includes providing a prognosis for progression, regression, recurrence, or disease-free survival of a medical condition based on the first physiological arterial parameter of the location on the extremity of the subject. In some implementations, the medical condition is peripheral arterial disease (PAD), critical limb ischemia, ulceration, gangrene, tissue ischemia, ulcer formation, ulcer progression, pressure ulcer formation, pressure ulcer progression, diabetic foot ulcer formation, diabetic foot ulcer progression, venous stasis, venous ulcer disease, infection, shock, cardiac decompensation, respiratory insufficiency, hypovolemia, the progression of diabetes, congestive heart failure, sepsis, dehydration, hemorrhage, hypertension, exposure to a chemical or biological agent, or an inflammatory response.

In some implementations, the method further includes assigning a therapy for a medical condition based on the first physiological arterial parameter of the location on the extremity of the subject. In some implementations, the medical condition is peripheral arterial disease (PAD), critical limb ischemia, ulceration, gangrene, tissue ischemia, ulcer formation, ulcer progression, pressure ulcer formation, pressure ulcer progression, diabetic foot ulcer formation, diabetic foot ulcer progression, venous stasis, venous ulcer disease, infection, shock, cardiac decompensation, respiratory insufficiency, hypovolemia, the progression of diabetes, congestive heart failure, sepsis, dehydration, hemorrhage, hypertension, exposure to a chemical or biological agent, or an inflammatory response.

In some embodiments, the method further includes providing a therapy for a medical condition based on the first physiological arterial parameter of the location on the extremity of the subject. In some implementations, the medical condition is peripheral arterial disease (PAD), critical limb ischemia, ulceration, gangrene, tissue ischemia, ulcer formation, ulcer progression, pressure ulcer formation, pressure ulcer progression, diabetic foot ulcer formation, diabetic foot ulcer progression, venous stasis, venous ulcer disease, infection, shock, cardiac decompensation, respiratory insufficiency, hypovolemia, the progression of diabetes, congestive heart failure, sepsis, dehydration, hemorrhage, hypertension, exposure to a chemical or biological agent, or an inflammatory response.

In some embodiments, the method further includes providing a preventative therapy for a medical condition based on the first physiological arterial parameter of the location on the extremity of the subject. For example, hyperspectral analysis of diabetic patients may identify hot spots indicating emerging foot ulcers that have not yet been ulcerated. In some implementations, the medical condition is peripheral arterial disease (PAD), critical limb ischemia, ulceration, gangrene, tissue ischemia, ulcer formation, ulcer progression, pressure ulcer formation, pressure ulcer progression, diabetic foot ulcer formation, diabetic foot ulcer progression, venous stasis, venous ulcer disease, infection, shock, cardiac decompensation, respiratory insufficiency, hypovolemia, the progression of diabetes, congestive heart failure, sepsis, dehydration, hemorrhage, hypertension, exposure to a chemical or biological agent, or an inflammatory response.

Exemplary Implementations

Figure 5:
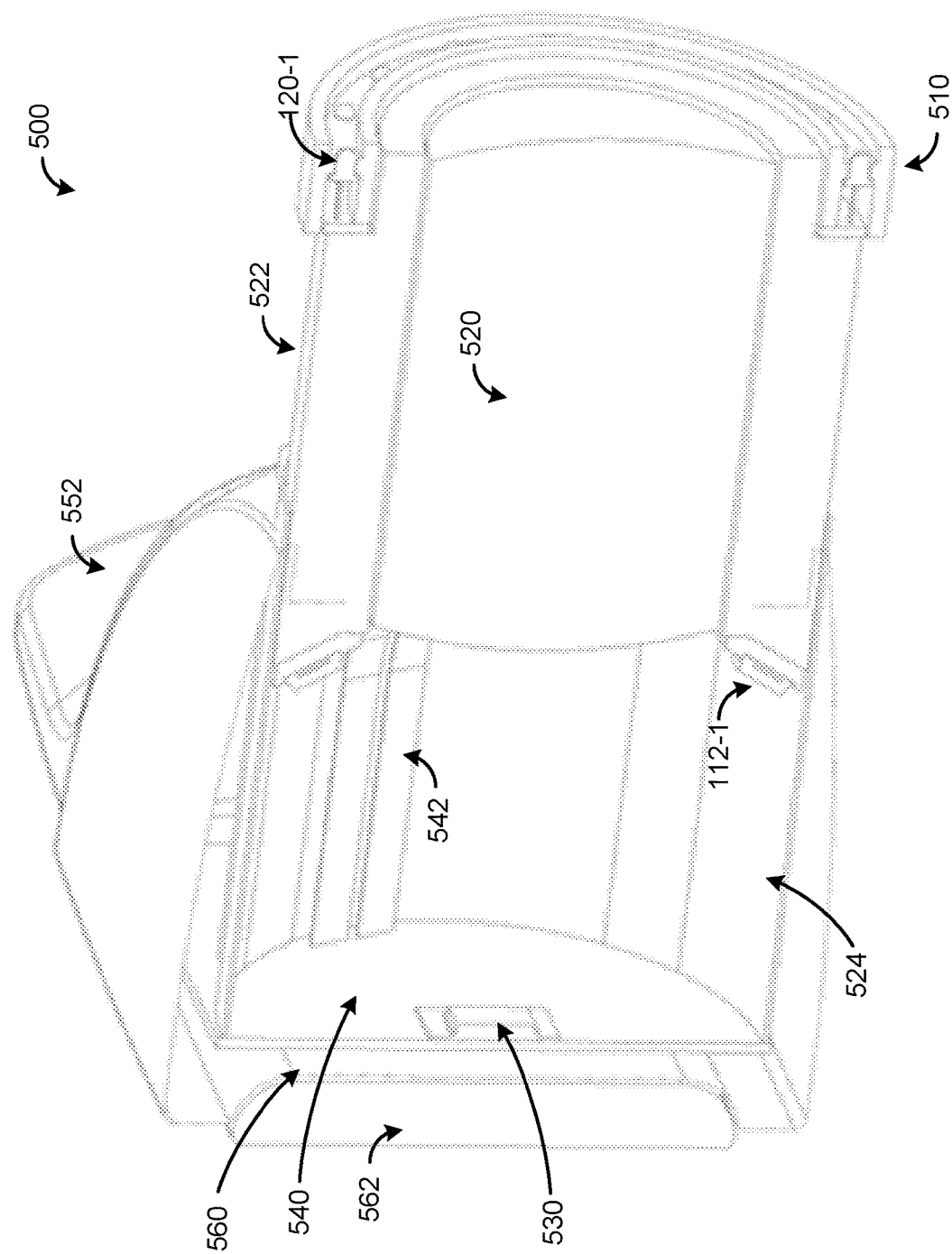
FIG. 5 is a schematic illustration of the internal hardware of a co-axial hyperspectral/multispectral camera mounted in a housing, according to some implementations. The illustration shows a cross-section down the barrel of the camera with a perspective view of the beam steering element 204.
Figure 6:
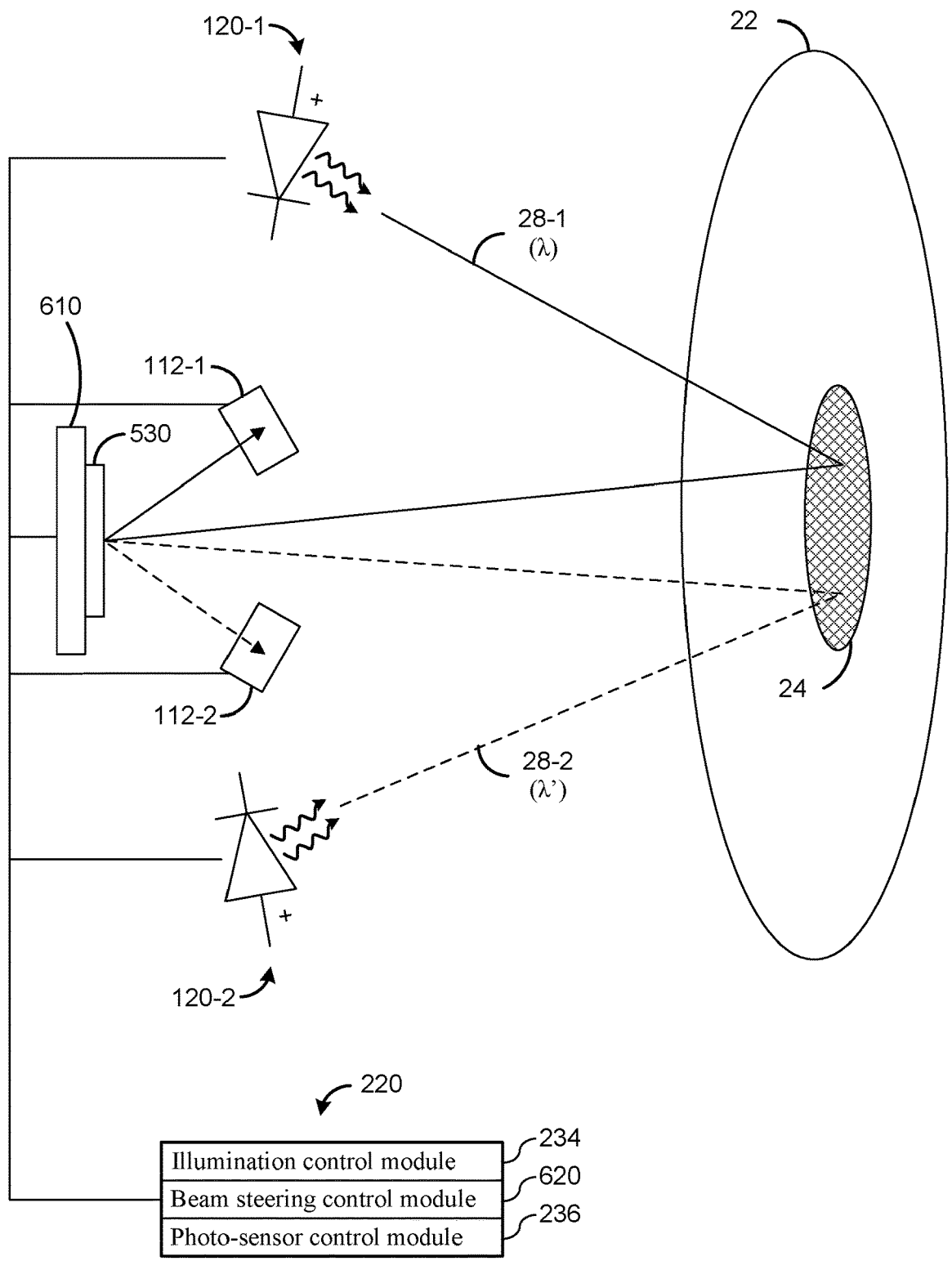
FIG. 6 is a schematic illustration of the light path for a captured hyperspectral/multispectral image, according to some implementations employing a co-axial hyperspectral imager with a beam-steering element.

In some implementations, the methods described herein are performed using imaging systems with unique internal optical architectures that allow for faster image acquisition and data processing. FIGS. 5 and 6 illustrate one such implementation in which the imaging system has a beam steering element configured to steer light to one of a plurality of optical detectors, each of which are configured to resolve light of a specific spectral band. FIG. 7 illustrates the principle behind a second such implementation, in which the imaging system employs a photo-sensor array having a plurality of photo-sensors, covered by a spectral filter array having a plurality of filter elements. This implementation enables capture of images at all wavelengths necessary to construct a hyperspectral image with a single exposure. FIG. 8 illustrates the principle behind a third such implementation, in which the imaging system simultaneously captures multiple images at multiple spectral bands by splitting the incidental light and directing it to multiple optical detectors.

FIG. 5 illustrates the use of an imaging system including a beam steering element having a plurality of operating modes, which directs light of different wavelengths to distinct optical detectors from a common point of origin, thus maintaining co-axial alignment between images captured by the respective optical detectors. In one implementation, the imaging device includes a housing having an exterior and an interior and at least one objective lens attached to or within the housing. The at least one objective lens is disposed in an optical communication path comprising an originating end and a terminating end. The imaging device also includes a beam steering element within the interior of the housing. The beam steering element is in optical communication with the at least one objective lens and is positioned at the terminating end of the optical communication path. The beam steering element is characterized by a plurality of operating modes. Each respective operating mode in the plurality of operating modes causes the beam steering element to be in optical communication with a different optical detector.

According to certain embodiments, the co-axial imaging device 500 includes: an illumination subsystem 510 containing one or more light sources 120; an objective lens assembly 520 housed in a chassis 522 that anchors the lens assembly with respect to other components of the optical assembly; an optional stray light shield 524; a beam steering element 530 in electrical communication, and optionally mounted on, a motherboard 540 in electrical communication with one or more CPU(s) (not shown); and an imager subsystem comprising a plurality of optical detectors 112 in electrical communication with the motherboard 540 by way of a flex circuit or wire 542.

In one embodiment, an optical communication path is created when radiation emitted from one or more of the lights 120 of the illumination subsystem 510 illuminates a tissue of the subject (not shown) and is backscattered to an objective lens assembly 520, which focuses the light on a beam steering element 530 having a plurality of operating modes. When positioned in a respective operating mode, the beam steering element 530 reflects the light onto one of the plurality of optical detectors 112, which is configured to capture an image of the surface of the subject at one or more specific wavelengths.

Each optical detector 112 in the imager subsystem is optionally covered by an optical filter (e.g., a detector filter), which allows light of a predetermined wavelength to pass through to the detector. In one embodiment, one or more of the light sources 120 is matched to a filter covering an optical detector 112, e.g., the light emits radiation at wavelength that is capable of passing through the corresponding filter. When respective light sources 120 in a plurality of light sources are matched to corresponding detector filters in a plurality of detector filters, the beam steering element 530 functions to direct radiation emitted by a respective light source 120 to the corresponding optical detector 112 covered by a matching filter. The beam steering element 530 is configured to have a plurality of operating modes, each of which directs light backscattered from the tissue of the subject to a different optical detector 112.

The internal hardware of co-axial imaging device 500 is mounted in housing 552, according to some embodiments. Optionally, housing 552 includes dock 560 for attaching portable device 562 to housing 552. Optionally, portable device 562 contains a display, preferably a touch-screen display, for displaying images acquired by internal hardware of a co-axial imaging device 500.

Referring to FIG. 6, light 28 having a first wavelength ($\lambda$), emitted from a light source 120, reflects or backscatters from a region of interest (24; ROI) on an object or subject 22. The light 28 then passes through the objective lens assembly (not shown) and is directed by a beam steering element 530, positioned in a first operating mode in a plurality of operating modes, towards an optical detector 112 configured to resolve light of the first wavelength ($\lambda$). In certain embodiments, the beam steering element is positioned in its respective operating modes through the use of an actuator 610 capable of adjust tip and tilt angles of the beam steering element.

In some embodiments, control modules, stored in the system memory 220 control: the illumination, via an illumination control module 234, the direction of the beam towards one or more optical detectors 112 via a beam steering control module 620, and the image exposure time and optical detectors themselves via an optical detector control module 236. The beam steering control module 620 directs actuator 610 to place the beam steering element 530 in various operating modes, each of which is in optical communication with one of the optical detectors 112.

For example, to collect images of an object 22 for hyperspectral/multispectral analysis at two different wavelengths, λ and λ', the illumination control module 234 turns on a first light 120-1, emitting light 28-1 at a first wavelength (λ), illuminating a region of interest (ROI) 24 on the subject 22. Reflected or backscattered light 120-1 from the subject 22 enters the objective lens or assembly thereof (not shown) and hits the beam steering element 530, placed in a first operating mode by an actuator 610 controlled by the beam steering control module 620, which redirects the light onto an optical detector 112-1 configured to resolve light of wavelength λ. The illumination control module 234 then turns off the first light 120-1 and turns on a second light 120-2, emitting light 28-2 at a second wavelength (λ'), illuminating the ROI 24. Concurrently, the beam steering control module 620 instructs the actuator 610 to place the beam steering element 530 in a second operating mode, which is in optical communication with a second optical detector 112-2 configured to resolve light of wavelength λ'. Thus, when reflected or backscattered light 28-2 hits the beam steering element 530, the light 28-2 is redirected onto the second optical detector 112-2.

The beam steering element 530 can be one or more reflective elements capable of redirecting the incident beam in one or more directions toward the detector(s). In some embodiments, the beam steering element 530 is an element that reflects light in one or more directions (e.g., a mirror element). In a particular embodiment the beam steering element is a plain mirror capable of reflecting light over a wide range of wavelengths. In another particular embodiment, the beam steering element is an array of mirrors, for example an array of micromirrors.

In one embodiment, the beam steering element consists of more than one element and is capable of simultaneously directing lights of different wavelengths in different directions. In specific embodiments, the beam steering element includes a first hot mirror and a second mirror positioned behind the hot mirror. The hot mirror is suitably coated to reflect light above or below a certain wavelength, while being transparent to light with lower or higher wavelengths, respectively.

Further implementations of the co-axial hyperspectral imaging strategy are disclosed in International Publication No. WO 2014/007869, the content of which is expressly incorporated herein by reference, in its entirety, for all purposes.

In some implementations, the method is performed using an imaging device including a photo-sensor array including a plurality of photo-sensors. Each photo-sensor provides a respective output. The device further comprises a spectral filter array having a plurality of filter elements. Each filter element is arranged to filter light received by a respective one or more of the photo-sensors. Each filter element is one of a plurality of filter-types. Each filter-type characterized by a unique spectral pass-band. The device further includes an interface module to select a plurality of subsets of photo-sensor outputs. Each such subset is associated with a single respective filter-type. The device comprises a control module that generates a hyperspectral data cube from the subsets of photo-sensor outputs by generating a plurality of images. Each such image is produced from a single corresponding subset of photo-sensor outputs in the plurality of photo-sensor outputs and so is associated with a corresponding filter-type in the plurality of filter-types.

FIG. 7 is an exploded schematic view of an implementation of an image sensor assembly for a single-sensor imaging device 700. The image sensor assembly includes a photo-sensory array 112 in combination with a filter array 114. In some implementations, the photo-sensory array 112 includes a plurality of photo-sensors. For example, detailed view 710 schematically shows, as a non-limiting example only, a number of photo-sensors 711 included in the photo-sensor array 112. Each photo-sensor 711 generates a respective electrical output by converting light incident on the photo-sensor.

The light incident on a particular photo-sensor 711 is filtered by a respective filter in the filter array 114. In some implementations, the filter array 114 is configured to include a plurality of filter elements. Each filter element is arranged to filter light received by a respective one or more of the plurality of photo-sensors in the photo-sensor array 112. Each filter element is also one of a plurality of filter-types, and each filter-type is characterized by a spectral pass-band different from the other filter-types. As such, the electrical output of a particular photo-sensor is associated with a particular spectral pass-band associated with the respective filter associated the particular photo-sensor 711.

For example, the detailed view 720 schematically shows, as a non-limiting example only, a number of filter-types A, B, C, D, E, F, G, H, and I are included in the filter array 114. In one implementation, at least two of filter types A, B, C, D, E, F, G, H, and I have different spectral pass-bands. For example, as illustrated in FIG. 7, filter elements 721a-1 and 721a-2 of filter types A and B, respectively, have different spectral pass-bands. In some implementations, at least two of filter types A, B, C, D, E, F, G, H, and I have the same spectral pass-band and at least two of filter types A, B, C, D, E, F, G, H, and I have different spectral pass-bands.

In some implementations, each filter-type A, B, C, D, E, F, G, H, and I has a spectral pass-band different from the others. In some implementations, the filter-types A, B, C, D, E, F, G, H, and I are arranged in a 3×3 grid that is repeated across the filter array 114. For example, as illustrated in FIG. 7, three filter elements 721a-1, 721b-1, 721c-1 of filter-type A are illustrated to show that instances of filter-type A are repeated in a uniform distribution across the filter array 114 such that the center-to-center distance d1 between two filters of the same type is less than 250 microns in some implementations. In some implementations, the center-to-center distance d1 between two filters of the same type is less than 100 microns.

Moreover, while nine filter-types are illustrated for example in FIG. 7, those skilled in the art will appreciate from the present disclosure that any number of filter types can be used in various implementations. For example, in some implementations 3, 5, 16 or 25 filter-types can be used in various implementations. Additionally and/or alternatively, while a uniform distribution of filter-types has been illustrated and described, those skilled in the art will appreciate from the present disclosure that, in various implementations, one or more filter-types may be distributed across a filter array in a non-uniform distribution. Additionally and/or alternatively, those skilled in the art will also appreciate that "white-light" or transparent filter elements may be included as one of the filter-types in a filter array.

FIG. 7 illustrates an advantage of the single-sensor imaging device. A single exposure of light 30 from a lens assembly is filtered by filter array 114 to form filtered light 32 that impinges upon sensor 112 and, from this single exposure, multiple images 243 of the same region 24 of a subject 22 are concurrently made. The imaging device 700 includes a photo-sensor array 112 including a plurality of photo-sensors 711. Each photo-sensor 711 provides a respective output. Imaging device 700 further includes a spectral filter array 114 having a plurality of filter elements 721. Each filter element 721 is arranged to filter light 30 received by a respective one or more of the plurality of photo-sensors 711. Each filter element 721 is one of a plurality of filter-types. For instance, in FIG. 7, each filter element 721 is one of filter types A, B, C, D, E, F, G, H, and I, with each respective filter-type characterized by a spectral pass-band different from the other filter-types.

An interface module selects one or more subsets of photo-sensor 711 outputs. Each subset of photo-sensor 711 outputs is associated with (receives light exclusively through) a single respective filter-type. For instance, in one such subset are the photo-sensors 711 that are associated with (receive light exclusively from) filter type A, another such subset are the photo-sensors 711 that are associated with filter type B and so forth. A control module is configured to generate a hyperspectral data cube 262 from the one or more sub-sets of photo-sensor outputs by generating a plurality of respective images 263. In some embodiments, each respective image 263 in the plurality of images is produced from a single respective sub-set of photo-sensor outputs 711 so that each respective image 263 in the plurality of images is associated with a particular filter-type. Thus, for example, referring to FIG. 7, all the photo-sensors 711 that receive filtered light from filter elements 721 of filter type A are used to form a first image 263-1, all the photo-sensors 711 that receive filtered light from filter elements 721 of filter type B are used to form a second image 263-2, all the photo-sensors 711 that receive filtered light from filter elements 721 of filter type C are used to form a third image 263-3, and so forth thereby creating a hyperspectral data cube 262 from the one or more sub-sets of photo-sensor outputs. The hyperspectral data cube 262 comprises the plurality of images, each image being of the same region of a subject but at a different wavelength or wavelength ranges.

The concept disclosed in FIG. 7 is highly advantageous because multiple light exposures do not need to be used to acquire all the images 263 needed to form the hyperspectral data cube 262. In some embodiments, a single light exposure is used to concurrently acquire each image 263. This is made possible because the spatial resolution of the sensor 112 exceeds the resolution necessary for an image 263. Thus, rather than using all the pixels in the sensor 112 to form each image 263, the pixels can be divided up in the manner illustrated in FIG. 7, for example, using filter plate 114 so that all the images are taken concurrently. In some implementations, the spectral pass-bands of the filter-elements used in a filter array 114 correspond to a predetermined set of spectral bands, e.g., used to identify a particular type of spectral signature in an object (e.g., in a tissue of a subject).

In one implementation, an imaging device comprises a filter array 114 containing a first set of filter elements sufficient to distinguish spectral signatures related to a first medical condition (e.g., a pressure ulcer from healthy tissue (e.g., non-ulcerated tissue). In one implementation, the filter array 114 of the imaging device further contains a second set of filter elements sufficient to distinguish spectral signatures related to a second medical condition (e.g., a cancerous tissue) from healthy tissue (e.g., a non-cancerous tissue). In some implementations, the first set of filter elements and the second set of filter elements may overlap, such that a particular filter element is used for investigation of both types of medical conditions. Accordingly, in some implementations, the imaging device will have a plurality of imaging modalities, each individual imaging modality related to the investigation of a different medical condition.

Further implementations of the single-sensor imaging device are disclosed in International Publication No. WO 2014/063117, the content of which is expressly incorporated herein by reference, in its entirety, for all purposes.

In some implementations, a similar effect can be achieved by placing multiple imager chips in an array (e.g., a 2×2, 3×3, 4×4, or 5×5 array). To minimize off axis imaging errors, individual imager dies may be arranged in a tight, multi-chip module configuration.

In some implementations, the method is performed using an imaging device that simultaneously captures multiple images, where each image represents a desired spectral band. Specifically, the imaging device uses multiple photo-sensors and beam splitting elements to capture a plurality of images simultaneously. Thus, a user does not need to maintain perfect alignment between the imaging device and a subject while attempting to capture multiple discrete images, and can instead simply align the imaging device once and capture all of the required images in a single operation of the imaging device.

FIG. 8 is an exploded schematic view of an optical assembly of an exemplary simultaneous capture imaging system, in accordance with some implementations, in which the optical paths formed by the optical path assembly are shown. In some implementations, the imager includes a single light source 120. In other implementations, as shown in FIG. 8, the imager contains two or more light sources 120, configured to emit light having different spectral bands (e.g., partially overlapping or non-overlapping). In some implementations, the light sources emit the same spectral bands, but are differentially filtered (e.g., by a filter placed in front of the light sources) such that the illuminating light from each light source has different spectral bands (e.g., partially overlapping or non-overlapping). The optical path assembly channels light received by the lens assembly 520 (e.g., illuminating light emitted from light source 120 and back-scattered from the region of interest on the patient) to the various photo-sensors 112 of the optical assembly.

Turning to FIG. 8, the optical assembly includes a first beam splitter 810-1, a second beam splitter 810-2, and a third beam splitter 810-3. Each beam splitter is configured to split the light received by the beam splitter into at least two optical paths. For example, beam splitters for use in the optical path assembly may split an incoming beam into one output beam that is collinear to the input beam, and another output beam that is perpendicular to the input beam.

Specifically, the first beam splitter 810-1 is in direct optical communication with the lens assembly 52, and splits the incoming light (represented by arrow 30) into a first optical path and a second optical path. The first optical path is substantially collinear with the light entering the first beam splitter 810-1, and passes to the second beam splitter 810-2. The second optical path is substantially perpendicular to the light entering the first beam splitter 810-1, and passes to the third beam splitter 810-3. In some implementations, the first beam splitter 810-1 is a 50:50 beam splitter. In other implementations, the first beam splitter 810-1 is a dichroic beam splitter.

The second beam splitter 810-2 is adjacent to the first beam splitter 810-1 (and is in direct optical communication with the first beam splitter 810-1), and splits the incoming light from the first beam splitter 810-1 into a third optical path and a fourth optical path. The third optical path is substantially collinear with the light entering the second beam splitter 810-2, and passes through to the first beam steering element 812-1. The fourth optical path is substantially perpendicular to the light entering the second beam splitter 810-2, and passes through to the second beam steering element 812-2. In some implementations, the second beam splitter 810-2 is a 50:50 beam splitter. In other implementations, the second beam splitter 810-2 is a dichroic beam splitter.

The beam steering elements 812 (e.g., 812-1 . . . 812-4) are configured to change the direction of the light that enters one face of the beam steering element. Beam steering elements 812 are any appropriate optical device that changes the direction of light. For example, in some implementations, the beam steering elements 812 are prisms (e.g., folding prisms or bending prisms). In some implementations, the beam steering elements 812 are mirrors. In some implementations, the beam steering elements 812 are other appropriate optical devices or combinations of devices.

Returning to FIG. 8, the first beam steering element 812-1 is adjacent to and in direct optical communication with the second beam splitter 810-2, and receives light from the third optical path (e.g., the output of the second beam splitter 810-2 that is collinear with the input to the second beam splitter 810-2). The first beam steering element 812-1 deflects the light in a direction that is substantially perpendicular to the fourth optical path (and, in some implementations, perpendicular to a plane defined by the optical paths of the beam splitters 212, e.g., the x-y plane) and onto the first photo-sensor 112-1. The output of the first beam steering element 214-1 is represented by arrow 31-1.

The second beam steering element 812-2 is adjacent to and in direct optical communication with the second beam splitter 810-2, and receives light from the fourth optical path (e.g., the perpendicular output of the second beam splitter 810-2). The second beam steering element 812-2 deflects the light in a direction that is substantially perpendicular to the third optical path (and, in some implementations, perpendicular to a plane defined by the optical paths of the beam splitters 810, e.g., the x-y plane) and onto the second photo-sensor 112-2. The output of the second beam steering element 812-2 is represented by arrow 31-2.

As noted above, the first beam splitter 810-1 passes light to the second beam splitter 810-2 along a first optical path (as discussed above), and to the third beam splitter 810-3 along a second optical path.

The third beam splitter 810-3 is adjacent to the first beam splitter 810-1 (and is in direct optical communication with the first beam splitter 810-1), and splits the incoming light from the first beam splitter 810-1 into a fifth optical path and a sixth optical path. The fifth optical path is substantially collinear with the light entering the third beam splitter 810-3, and passes through to the third beam steering element 812-3. The sixth optical path is substantially perpendicular to the light entering the third beam splitter 810-3, and passes through to the fourth beam steering element 812-4. In some implementations, the third beam splitter 810-3 is a 50:50 beam splitter. In other implementations, the third beam splitter 810-3 is a dichroic beam splitter.

The third beam steering element 812-3 is adjacent to and in direct optical communication with the third beam splitter 810-3, and receives light from the fifth optical path (e.g., the output of the third beam splitter 810-3 that is collinear with the input to the third beam splitter 810-3). The third beam steering element 812-3 deflects the light in a direction that is substantially perpendicular to the third optical path (and, in some implementations, perpendicular to a plane defined by the optical paths of the beam splitters 810, e.g., the x-y plane) and onto the third photo-sensor 112-3. The output of the third beam steering element 812-3 is represented by arrow 31-3.

The fourth beam steering element 812-4 is adjacent to and in direct optical communication with the third beam splitter 810-3, and receives light from the sixth optical path (e.g., the perpendicular output of the third beam splitter 810-3). The fourth beam steering element 812-4 deflects the light in a direction that is substantially perpendicular to the sixth optical path (and, in some implementations, perpendicular to a plane defined by the optical paths of the beam splitters 810, e.g., the x-y plane) and onto the fourth photo-sensor 112-4. The output of the fourth beam steering element 812-4 is represented by arrow 31-4.

As shown in FIG. 8, the output paths of the first and third beam steering elements 812-1, 812-3 are in opposite directions than the output paths of the second and fourth beam steering elements 812-2, 812-4. Thus, the image captured by the lens assembly 520 is projected onto the photo-sensors mounted on the opposite sides of the image assembly. However, the beam steering elements 812 need not face these particular directions. Rather, any of the beam steering elements 812 can be positioned to direct the output path of each beam steering element 812 in any appropriate direction. For example, in some implementations, all of the beam steering elements 812 direct light in the same direction. In such cases, all of the photo-sensors may be mounted on a single circuit board. Alternatively, in some implementations, one or more of the beam steering elements 812 directs light substantially perpendicular to the incoming light, but in substantially the same plane defined by the optical paths of the beam splitters 810 (e.g., within the x-y plane).

Further implementations of the single-sensor hyperspectral imaging strategy are disclosed in U.S. Non-Provisional application Ser. No. 14/664,754, entitled "Compact Light Sensor, filed Mar. 20, 2015, the content of which is expressly incorporated herein by reference, in its entirety, for all purposes.

Hyperspectral Imaging

Hyperspectral and multispectral imaging are related techniques in larger class of spectroscopy commonly referred to as spectral imaging or spectral analysis. Typically, hyperspectral imaging relates to the acquisition of a plurality of images, each image representing a narrow spectral band collected over a continuous spectral range, for example, 5 or more (e.g., 5, 10, 15, 20, 25, 30, 40, 50, or more) spectral bands having a FWHM bandwidth of 1 nm or more each (e.g., 1 nm, 2 nm, 3 nm, 4 nm, 5 nm, 10 nm, 20 nm or more), covering a contiguous spectral range (e.g., from 400 nm to 800 nm). In contrast, multispectral imaging relates to the acquisition of a plurality of images, each image representing a narrow spectral band collected over a discontinuous spectral range.

For the purposes of the present disclosure, the terms "hyperspectral" and "multispectral" are used interchangeably and refer to a plurality of images, each image representing a narrow spectral band, whether collected over a continuous or discontinuous spectral range. For example, in some implementations, wavelengths 1-N of a hyperspectral data cube 1336-1 are contiguous wavelengths or spectral bands covering a contiguous spectral range (e.g., from 400 nm to 800 nm). In other implementations, wavelengths 1-N of a hyperspectral data cube 1336-1 are non-contiguous wavelengths or spectral bands covering a non-contiguous spectral ranges (e.g., from 400 nm to 440 nm, from 500 nm to 540 nm, from 600 nm to 680 nm, and from 900 to 950 nm).

As used herein, a "narrow spectral range," "narrow spectral band," and "narrowband radiation" refer to a continuous span of wavelengths (e.g., a band), typically consisting of a FWHM spectral band of no more than about 100 nm. In certain embodiments, narrowband radiation consists of a FWHM spectral band of no more than about 75 nm, 50 nm, 40 nm, 30 nm, 25 nm, 20 nm, 15 nm, 10 nm, 5 nm, 4 nm, 3 nm, 2 nm, 1 nm, or less. In some implementations, the narrowband radiation has a FWHM of about 100 nm, 75 nm, 50 nm, 40 nm, 30 nm, 25 nm, 20 nm, 15 nm, 10 nm, 5 nm, 4 nm, 3 nm, 2 nm, 1 nm, or less. In some implementations, the narrowband radiation has a FWHM spectral band of between 1 and 100 nm, for example, from 1 to 50 nm, from 1 to 25 nm, from 1 to 10 nm, from 1 to 5 nm, from 5 to 100 nm, from 5 to 50 nm, from 5 to 25 nm, or from 5 to 10 nm.

In some implementations, wavelengths imaged by the methods and devices disclosed herein are selected from one or more of the visible, near-infrared, short-wavelength infrared, mid-wavelength infrared, long-wavelength infrared, and ultraviolet (UV) spectrums.

By "broadband" it is meant light that includes component wavelengths over a substantial portion of at least one band, e.g., over at least 20%, or at least 30%, or at least 40%, or at least 50%, or at least 60%, or at least 70%, or at least 80%, or at least 90%, or at least 95% of the band, or even the entire band, and optionally includes component wavelengths within one or more other bands. A "white light source" is considered to be broadband, because it extends over a substantial portion of at least the visible band. In certain embodiments, broadband light includes component wavelengths across at least 100 nm of the electromagnetic spectrum. In other embodiments, broadband light includes component wavelengths across at least 150 nm, 200 nm, 250 nm, 300 nm, 400 nm, 500 nm, 600 nm, 700 nm, 800 nm, or more of the electromagnetic spectrum.

By "narrowband" it is meant light that includes components over only a narrow spectral region, e.g., less than 20%, or less than 15%, or less than 10%, or less than 5%, or less than 2%, or less than 1%, or less than 0.5% of a single band. Narrowband light sources need not be confined to a single band, but can include wavelengths in multiple bands. A plurality of narrowband light sources may each individually generate light within only a small portion of a single band, but together may generate light that covers a substantial portion of one or more bands, e.g., may together constitute a broadband light source. In certain embodiments, broadband light includes component wavelengths across no more than 100 nm of the electromagnetic spectrum (e.g., has a spectral bandwidth of no more than 100 nm). In other embodiments, narrowband light has a spectral bandwidth of no more than 90 nm, 80 nm, 75 nm, 70 nm, 60 nm, 50 nm, 40 nm, 30 nm, 25 nm, 20 nm, 15 nm, 10 nm, 5 nm, or less of the electromagnetic spectrum.

As used herein, the "spectral bandwidth" of a light source refers to the span of component wavelengths having an intensity that is at least half of the maximum intensity, otherwise known as "full width at half maximum" (FWHM) spectral bandwidth. Many light emitting diodes (LEDs) emit radiation at more than a single discreet wavelength, and are thus narrowband emitters. Accordingly, a narrowband light source can be described as having a "characteristic wavelength" or "center wavelength," i.e., the wavelength emitted with the greatest intensity, as well as a characteristic spectral bandwidth, e.g., the span of wavelengths emitted with an intensity of at least half that of the characteristic wavelength.

By "coherent light source" it is meant a light source that emits electromagnetic radiation of a single wavelength in phase. Thus, a coherent light source is a type of narrowband light source with a spectral bandwidth of less than 1 nm. Non-limiting examples of coherent light sources include lasers and laser-type LEDs. Similarly, an incoherent light source emits electromagnetic radiation having a spectral bandwidth of more than 1 nm and/or is not in phase. In this regard, incoherent light can be either narrowband or broadband light, depending on the spectral bandwidth of the light.

Examples of suitable broadband light sources 106 include, without limitation, incandescent lights such as a halogen lamp, xenon lamp, a hydrargyrum medium-arc iodide lamp, and a broadband light emitting diode (LED). In some embodiments, a standard or custom filter is used to balance the light intensities at different wavelengths to raise the signal level of certain wavelength or to select for a narrowband of wavelengths. Broadband illumination of a subject is particularly useful when capturing a color image of the subject or when focusing the hyperspectral/multispectral imaging system.

Examples of suitable narrowband, incoherent light sources 106 include, without limitation, a narrow band light emitting diode (LED), a superluminescent diode (SLD) (see, Redding B., arVix: 1110.6860 (2011), the content of which is hereby incorporated herein by reference in its entirety for all purposes), a random laser, and a broadband light source covered by a narrow band-pass filter. Examples of suitable narrowband, coherent light sources 104 include, without limitation, lasers and laser-type light emitting diodes. While both coherent and incoherent narrowband light sources 104 can be used in the imaging systems described herein, coherent illumination is less well suited for full-field imaging due to speckle artifacts that corrupt image formation (see, Oliver, B. M., *Proc IEEE* 51, 220-221 (1963)).

It will also be understood that, although the terms "first," "second," etc. may be used herein to describe various elements, these elements should not be limited by these terms. These terms are only used to distinguish one element from another. For example, a first contact could be termed a second contact, and, similarly, a second contact could be termed a first contact, which changing the meaning of the description, so long as all occurrences of the "first contact" are renamed consistently and all occurrences of the second contact are renamed consistently. The first contact and the second contact are both contacts, but they are not the same contact.

The terminology used herein is for the purpose of describing particular embodiments only and is not intended to be limiting of the claims. As used in the description of the embodiments and the appended claims, the singular forms "a", "an" and "the" are intended to include the plural forms as well, unless the context clearly indicates otherwise. It will also be understood that the term "and/or" as used herein refers to and encompasses any and all possible combinations of one or more of the associated listed items. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

As used herein, the term "if" may be construed to mean "when" or "upon" or "in response to determining" or "in accordance with a determination" or "in response to detecting," that a stated condition precedent is true, depending on the context. Similarly, the phrase "if it is determined [that a stated condition precedent is true]" or "if [a stated condition precedent is true]" or "when [a stated condition precedent is true]" may be construed to mean "upon determining" or "in response to determining" or "in accordance with a determination" or "upon detecting" or "in response to detecting" that the stated condition precedent is true, depending on the context.

The foregoing description, for purpose of explanation, has been described with reference to specific embodiments. However, the illustrative discussions above are not intended to be exhaustive or to limit the invention to the precise forms disclosed. Many modifications and variations are possible in view of the above teachings. The embodiments were chosen and described in order to best explain the principles of the invention and its practical applications, to thereby enable others skilled in the art to best utilize the invention and various embodiments with various modifications as are suited to the particular use contemplated.

What is claimed is:

1. An electronic device, comprising:
   one or more optical detectors configured to acquire a plurality of images, wherein each respective image in the plurality of images is collected at a unique spectral band in a predetermined set of spectral bands;
   one or more processors; and
   memory, the memory storing one or more programs configured to be executed by the one or more processors, the one or more programs comprising instructions, responsive to operation by a medical professional associated with a business entity, wherein the medical professional is associated with a temporal clinical expenditure cost, for:
   collecting the plurality of images of a location on an extremity of a subject with the one or more optical detectors in accordance with a current procedural terminology code;
   registering the plurality of images with respect to each other thereby forming a plurality of registered images;
   determining a first physiologic arterial parameter of the location on the extremity of the subject from the plurality of registered images;
   creating a record of the first physiological arterial parameter of the location on the extremity of the subject; and
   outputting an indication of the first physiologic arterial parameter of the location on the extremity of the subject, wherein
   the collecting, registering, determining, creating, and outputting (i) perform at least a subset of actions required by the current procedural terminology code and (ii) are subject to a constraint $$(D^*E_D) < (R_C - I_c)$$

wherein,
D is a duration of an epoch,
$E_D$ is the temporal clinical expenditure cost prorated for the duration of the epoch,
$R_C$ is an average or absolute amount of reimbursement associated with the current procedural terminology code that is receivable by the business entity, and
$I_C$ is an incidental expenditure, other than $R_C$, associated with the medical professional using the electronic device to perform actions required by the current procedural terminology code.

2. The electronic device of clam 1, wherein the first physiologic arterial parameter is a two-dimensional map of deoxyhemoglobin concentration, oxyhemoglobin concentration, or an arithmetic combination of deoxyhemoglobin and oxyhemoglobin concentration of the location on the extremity of the subject.

3. The electronic device of claim 1, wherein
   the electronic device further comprises one or more communication interfaces in electrical communication with the memory, and
   the instructions for creating the record of the first physiological arterial parameter comprises instructions for transmitting, via the one or more communication interfaces, the record to an electronic data store external to the electronic device.

4. The electronic device of claim 1, wherein
   the one or more optical detectors, the one or more processors, and the memory are housed in a casing,
   the electronic device further comprises a display mounted on an exterior of the casing, and
   the instructions for outputting the indication of the first physiologic arterial parameter comprises instructions for displaying the indication on the display.

5. The electronic device of claim 1, wherein the current procedural terminology code is selected from:
   (i) a medical code associated with a noninvasive single level, bilateral physiologic study of upper or lower extremity arteries;
   (ii) a noninvasive multiple level, complete bilateral physiologic study of upper or lower extremity arteries; and
   (iii) a noninvasive physiologic study of lower extremity arteries, at rest following treadmill stress testing.

6. The electronic device of claim 1, wherein the predetermined set of spectral bands consists of from eight to twelve spectral bands.

7. The electronic device of claim 6, wherein the from eight to twelve spectral bands comprises eight spectral bands having central wavelengths of:
   (i) 510±1 nm, 530±1 nm, 540±1 nm, 560±1 nm, 580±1 nm, 590±1 nm, 620±1 nm, and 660±1 nm;
   (ii) 520±1 nm, 540±1 nm, 560±1 nm, 580±1 nm, 590±1 nm, 610±1 nm, 620±1 nm, and 640±1 nm; or
   (iii) 500±1 nm, 530±1 nm, 545±1 nm, 570±1 nm, 585±1 nm, 600±1 nm, 615±1 nm, and 640±1 nm, and
   wherein each respective spectral band in the eight spectral bands has a full width at half maximum of less than 10 nm.

8. The electronic device of clam 1, further comprising:
   one or more light sources, the one or more light sources configured to emit a first light, the first light encompassing a first subset of the predetermined set of spectral bands; and
   wherein the instructions for collecting the plurality of images comprises instructions for:
   illuminating the location on the extremity of the subject with the first light; and
   concurrently collecting, with the one or more optical detectors, a first subset of images in the plurality of images of the location on the extremity of the subject while illuminated by the first light, each respective image in the first subset of images collected at a unique spectral band in the first subset of the predetermined set of spectral bands.

9. The electronic device of claim 8, wherein:
   the one or more optical detectors comprises a plurality of optical detectors; and each respective image in the first subset of images is collected with a different optical detector in the plurality of optical detectors.

10. The electronic device of claim 8, wherein:
the one or more light sources are further configured to emit a second light, the second light comprising a second subset of spectral bands in the predetermined set of spectral bands, wherein the second subset of spectral bands is other than the first subset of spectral bands, and
the instructions for collecting the plurality of images further comprises instructions for:
illuminating the location on the extremity of the subject with the second light; and
concurrently collecting, with the one or more optical detectors, a second subset of images in the plurality of images of the location on the extremity of the subject while illuminated by the second light, each respective image in the second subset of images collected at a unique spectral band in the second subset of spectral bands.

11. The electronic device of claim 10, wherein:
the one or more optical detectors comprises a plurality of optical detectors,
each respective image in the first subset of images is collected with a different optical detector in the plurality of optical detectors,
each respective image in the second subset of images is collected with different optical detector in the plurality of optical detectors, and
at least one optical detector in the plurality of optical detectors collects a respective image in the first subset of images and a respective image in the second subset of images.

12. The electronic device of claim 11, wherein each respective optical detector in the plurality of optical detectors is covered by a corresponding dual bandpass filter in a plurality of dual bandpass filters.

13. The electronic device of claim 11, wherein each respective optical detector in the plurality of optical detectors collects a respective image in the first subset of images and a respective image in the second subset of images.

14. The electronic device of claim 13, wherein the first subset of images consists of four images and the second subset of images consists of four images.

15. A method comprising:
at an imaging system:
collecting a plurality of images of a location on an extremity of a subject with the imaging system, wherein each respective image in the plurality of images is collected by the imaging system at a unique spectral band in a predetermined set of spectral bands;
registering the plurality of images with respect to each other thereby forming a plurality of registered images;
determining a first physiologic arterial parameter of the location on the extremity of the subject from the plurality of registered images;
creating a record of the first physiological arterial parameter of the location on the extremity of the subject in an electronic data store; and
outputting an indication of the first physiologic arterial parameter of the location on the extremity of the subject,
wherein the method is performed by a medical professional in an epoch using the imaging system,
the medical professional is associated with a temporal clinical expenditure cost, and an expression $$(D*E_D)<(R_C-I_C)$$

is achieved, wherein,
D is a duration of the epoch,
$E_D$ is the temporal clinical expenditure cost prorated for the duration of the epoch,
$R_C$ is an average or absolute amount of reimbursement associated with a current procedural terminology code that is receivable by a business entity, and
$I_C$ is an incidental expenditure, other than $R_C$, associated with the medical professional using an electronic device to perform actions required by the current procedural terminology code.

16. The method of clam 15, wherein collecting the plurality of images comprises:
illuminating the location on the extremity of the subject with a first light, the first light encompassing a first subset of spectral bands in the predetermined set of spectral bands; and
concurrently collecting a first subset of images in the plurality of images of the location on the extremity of the subject while illuminated by the first light, each respective image in the first subset of images collected at a unique spectral band in the first subset of the spectral bands in the predetermined set of spectral bands.

17. The method of claim 16, wherein the first subset of spectral bands comprises all of the predetermined set of spectral bands.

18. The method of claim 16, wherein each respective image in the first subset of images is collected with a unique optical detector in a plurality of optical detectors.

19. The method of claim 16, wherein collecting the plurality of images further comprises:
illuminating the location on the extremity of the subject with a second light, the second light encompassing a second subset of spectral bands in the predetermined set of spectral bands, wherein the second subset of spectral bands is other than the first subset of spectral bands; and
concurrently collecting a second subset of images in the plurality of images of the location on the extremity of the subject while illuminated by the second light, each respective image in the second subset of images collected at a unique spectral band in the second subset of spectral bands.

20. The method of claim 19, wherein:
each respective image in the first subset of images is collected with a unique optical detector in a plurality of optical detectors,
each respective image in the second subset of images is collected with a unique optical detector in the plurality of optical detectors; and
at least one optical detector in the plurality of optical detectors collects a respective image in the first subset of images and a respective image in the second subset of images.

* * * * *